US010571715B2

(12) United States Patent
Rizzo, III et al.

(10) Patent No.: US 10,571,715 B2
(45) Date of Patent: Feb. 25, 2020

(54) ADAPTIVE VISUAL ASSISTIVE DEVICE

(71) Applicants: MASSACHUSETTS EYE & EAR INFIRMARY, Boston, MA (US); THE UNITED STATES GOVERNMENT AS REPRESENTED BY THE DEPARTMENT OF VETERANS AFFAIRS, Washington, DC (US)

(72) Inventors: Joseph F. Rizzo, III, Newton, MA (US); Attila Priplata, Arlington, MA (US); Minnan Xu, Cambridge, MA (US); Conrad Wall, III, Boston, MA (US)

(73) Assignees: Massachusetts Eye and Ear Infirmary, Boston, MA (US); The United States Government As Represented By The Department Of Veterans Affairs, Washington, DC (US)

(*) Notice: Subject to any disclaimer, the term of this patent is extended or adjusted under 35 U.S.C. 154(b) by 361 days.

(21) Appl. No.: 14/356,071

(22) PCT Filed: Nov. 5, 2012

(86) PCT No.: PCT/US2012/063619
§ 371 (c)(1),
(2) Date: Jan. 9, 2015

(87) PCT Pub. No.: WO2013/067539
PCT Pub. Date: May 10, 2013

(65) Prior Publication Data
US 2015/0002808 A1 Jan. 1, 2015

Related U.S. Application Data

(60) Provisional application No. 61/555,930, filed on Nov. 4, 2011, provisional application No. 61/555,908, filed on Nov. 4, 2011.

(51) Int. Cl.
G02C 5/00 (2006.01)
G02B 27/64 (2006.01)
(Continued)

(52) U.S. Cl.
CPC ............... *G02C 5/001* (2013.01); *A61F 9/08* (2013.01); *A61H 3/061* (2013.01);
(Continued)

(58) Field of Classification Search
CPC .. G02C 5/001; A61F 9/08; A61H 3/06; A61N 1/36046
(Continued)

(56) References Cited

U.S. PATENT DOCUMENTS 3,383,682 A 5/1968 Stephens, Jr.
4,712,003 A * 12/1987 Ban .......................... A61F 9/08
250/215
(Continued)

FOREIGN PATENT DOCUMENTS

CN 101076841 11/2007
CN 200984304 12/2007
(Continued)

OTHER PUBLICATIONS

Chinese Office Action in Chinese Application No. 201280066158.8, dated Oct. 8, 2015, 28 pages (with English Translation).
(Continued)

Primary Examiner — Kristina M Deherrera
(74) Attorney, Agent, or Firm — Fish & Richardson P.C.

(57) ABSTRACT

The disclosure features visual assistive devices that include a detection apparatus configured to receive information about an environment surrounding a user of the visual assistive device, a communication apparatus configured to transmit information to the user, and an electronic processor coupled to the detection apparatus and the communication apparatus, and configured to: receive information about an activity of the user; filter the information about the environment surrounding the user based on the activity of the user; assign a priority rank to each element of the filtered
(Continued)

information based on the activity of the user; and transmit at least some of the elements of the filtered information, according to the assigned priority ranks, to the user using the communication apparatus.

29 Claims, 11 Drawing Sheets

(51) Int. Cl.
   *H04N 5/232* (2006.01)
   *A61H 3/06* (2006.01)
   *A61N 1/36* (2006.01)
   *A61F 9/08* (2006.01)
   *G02C 11/00* (2006.01)

(52) U.S. Cl.
   CPC ....... *A61N 1/36046* (2013.01); *G02B 27/646* (2013.01); *G02C 11/10* (2013.01); *H04N 5/23258* (2013.01); *H04N 5/23267* (2013.01); *H04N 5/23287* (2013.01); *A61H 2201/0184* (2013.01); *A61H 2201/165* (2013.01); *A61H 2201/501* (2013.01); *A61H 2201/503* (2013.01); *A61H 2201/5007* (2013.01); *A61H 2201/5048* (2013.01); *A61H 2201/5069* (2013.01); *A61H 2201/5079* (2013.01); *A61H 2201/5084* (2013.01); *A61H 2201/5092* (2013.01); *A61H 2201/5097* (2013.01); *G03B 2205/0007* (2013.01); *G03B 2217/005* (2013.01); *H04N 5/23261* (2013.01)

(58) Field of Classification Search
   USPC .............................. 351/158; 607/53, 54, 141
   See application file for complete search history.

(56) References Cited

U.S. PATENT DOCUMENTS

| | | |
|---|---|---|
| 4,992,998 A | 2/1991 | Woodward |
| 5,159,927 A | 11/1992 | Schmid |
| 5,411,540 A | 5/1995 | Edell et al. |
| 5,476,494 A | 12/1995 | Edell et al. |
| 5,521,957 A | 5/1996 | Hansen |
| 5,554,187 A | 9/1996 | Rizzo, III |
| 5,575,813 A | 11/1996 | Edell et al. |
| 5,597,381 A | 1/1997 | Rizzo, III |
| 5,636,038 A | 6/1997 | Lynt et al. |
| 5,642,431 A | 6/1997 | Poggio et al. |
| 5,777,715 A | 7/1998 | Kruegle et al. |
| 5,800,530 A | 9/1998 | Rizzo, III |
| 5,835,616 A | 11/1998 | Lobo et al. |
| 5,850,470 A | 12/1998 | Kung et al. |
| 5,875,018 A | 2/1999 | Lamprecht |
| 5,935,155 A | 8/1999 | Humayun et al. |
| 6,104,671 A | 8/2000 | Hoyt et al. |
| 6,115,482 A | 9/2000 | Sears et al. |
| 6,120,538 A | 9/2000 | Rizzo, III et al. |
| 6,161,091 A | 12/2000 | Akamine et al. |
| 6,230,057 B1 | 5/2001 | Chow et al. |
| 6,324,429 B1 | 11/2001 | Shire et al. |
| 6,368,349 B1 | 4/2002 | Wyatt et al. |
| 6,389,317 B1 | 5/2002 | Chow et al. |
| 6,411,327 B1 | 6/2002 | Kweon et al. |
| 6,446,041 B1 | 9/2002 | Reynar et al. |
| 6,470,264 B2 | 10/2002 | Bide |
| 6,549,122 B2 | 4/2003 | Depta |
| 6,671,618 B2 | 12/2003 | Hoisko |
| 6,774,788 B1 | 8/2004 | Balfe |
| 6,920,358 B2 | 7/2005 | Greenberg et al. |
| 6,948,937 B2 | 9/2005 | Tretiakoff et al. |
| 6,976,998 B2 | 12/2005 | Rizzo et al. |
| 7,295,872 B2 | 11/2007 | Kelly et al. |
| 7,307,575 B2 | 12/2007 | Zemany |
| 7,308,315 B2 | 12/2007 | Ohta et al. |
| 7,565,139 B2 | 7/2009 | Neven, Sr. et al. |
| 7,598,976 B2 | 10/2009 | Sofer et al. |
| 7,627,142 B2 | 12/2009 | Kurzweil et al. |
| 7,642,949 B2 | 1/2010 | Pergande et al. |
| 7,659,915 B2 | 2/2010 | Kurzweil et al. |
| 7,782,251 B2 | 8/2010 | Bishop et al. |
| 7,788,032 B2 | 8/2010 | Moloney |
| 7,805,307 B2 | 9/2010 | Levin et al. |
| 7,817,855 B2 | 10/2010 | Yuille et al. |
| 7,898,468 B2 | 3/2011 | Samaniego et al. |
| 7,925,354 B2 | 4/2011 | Greenberg et al. |
| 7,965,196 B2 | 6/2011 | Liebermann |
| 7,967,439 B2 | 6/2011 | Shelhamer et al. |
| 7,983,920 B2 | 7/2011 | Sinclair, II |
| 7,991,576 B2 | 8/2011 | Roumeliotis |
| 8,009,928 B1 | 8/2011 | Manmatha et al. |
| 8,014,604 B2 | 9/2011 | Tzadok et al. |
| 8,015,132 B2 | 9/2011 | Xu |
| 8,018,580 B2 | 9/2011 | Luo et al. |
| 8,019,428 B2 | 9/2011 | Greenberg et al. |
| 8,021,045 B2 | 9/2011 | Foos et al. |
| 8,036,895 B2 | 10/2011 | Kurzweil et al. |
| 8,049,680 B2 | 11/2011 | Spruck et al. |
| 8,068,644 B2 | 11/2011 | Tkacik |
| 8,113,841 B2 | 2/2012 | Rojas et al. |
| 8,115,831 B2 | 2/2012 | Rodriquez et al. |
| 8,130,262 B2 | 3/2012 | Behm et al. |
| 8,135,217 B2 | 3/2012 | Goktekin et al. |
| 8,135,227 B2 | 3/2012 | Lewis et al. |
| 8,139,894 B2 | 3/2012 | Nestares |
| 8,150,107 B2 | 4/2012 | Kurzweil et al. |
| 8,154,771 B2 | 4/2012 | Albrecht et al. |
| 8,160,880 B2 | 4/2012 | Albrecht et al. |
| 8,174,931 B2 | 5/2012 | Vartanian et al. |
| 8,175,802 B2 | 5/2012 | Forstall et al. |
| 8,185,398 B2 | 5/2012 | Anderson et al. |
| 8,186,581 B2 | 5/2012 | Kurzweil et al. |
| 8,204,684 B2 | 6/2012 | Forstall et al. |
| 8,208,729 B2 | 6/2012 | Foss |
| 8,210,848 B1 | 7/2012 | Beck et al. |
| 8,218,020 B2 | 7/2012 | Tenchio et al. |
| 8,218,873 B2 | 7/2012 | Boncyk et al. |
| 8,218,874 B2 | 7/2012 | Boncyk et al. |
| 8,224,078 B2 | 7/2012 | Boncyk et al. |
| 8,224,079 B2 | 7/2012 | Boncyk et al. |
| 8,233,671 B2 | 7/2012 | Anderson et al. |
| 8,234,277 B2 | 7/2012 | Thong et al. |
| 8,239,032 B2 | 8/2012 | Dewhurst |
| 2001/0056342 A1 | 12/2001 | Piehn et al. |
| 2002/0111739 A1 | 8/2002 | Jandrell |
| 2003/0179133 A1 | 9/2003 | Pepin et al. |
| 2004/0107010 A1 | 6/2004 | King |
| 2005/0251223 A1 | 11/2005 | Eckmiller |
| 2006/0050933 A1 | 3/2006 | Adam et al. |
| 2006/0129308 A1 | 6/2006 | Kates |
| 2007/0025512 A1 | 2/2007 | Gertsenshteyn et al. |
| 2007/0211947 A1 | 9/2007 | Tkacik |
| 2007/0272738 A1 | 11/2007 | Berkun |
| 2007/0273708 A1 | 11/2007 | Andreasson et al. |
| 2007/0279497 A1 | 12/2007 | Wada |
| 2008/0037727 A1 | 2/2008 | Sivertsen et al. |
| 2008/0077196 A1 | 3/2008 | Greenberg et al. |
| 2008/0120029 A1 | 5/2008 | Zelek et al. |
| 2008/0136923 A1 | 6/2008 | Inbar et al. |
| 2008/0154336 A1 | 6/2008 | McClure et al. |
| 2008/0154337 A1 | 6/2008 | McClure et al. |
| 2008/0187104 A1 | 8/2008 | Sung et al. |
| 2008/0275527 A1 | 11/2008 | Greenberg et al. |
| 2008/0288067 A1 | 11/2008 | Flood |
| 2009/0002500 A1 | 1/2009 | Kawai |
| 2009/0186321 A1 | 7/2009 | Rojas et al. |
| 2009/0306741 A1 | 12/2009 | Hogle et al. |
| 2009/0312817 A1 | 12/2009 | Hogle et al. |
| 2010/0002204 A1 | 1/2010 | Jung et al. |
| 2010/0013612 A1 | 1/2010 | Zachman |
| 2010/0177179 A1 | 7/2010 | Behm et al. |
| 2010/0201793 A1 | 8/2010 | Kurzweil et al. |
| 2011/0013896 A1 | 1/2011 | Kawahara |

(56) References Cited

U.S. PATENT DOCUMENTS

| | | |
|---|---|---|
| 2011/0034176 A1 | 2/2011 | Lord et al. |
| 2011/0043644 A1 | 2/2011 | Munger et al. |
| 2011/0050546 A1 | 3/2011 | Swartz, Jr. et al. |
| 2011/0091098 A1 | 4/2011 | Yuille et al. |
| 2011/0092249 A1 | 4/2011 | Evanitsky |
| 2011/0143816 A1 | 6/2011 | Fischer et al. |
| 2011/0181745 A1 | 7/2011 | Nagatsuma et al. |
| 2011/0213664 A1 | 9/2011 | Osterhout et al. |
| 2011/0214082 A1 | 9/2011 | Osterhout et al. |
| 2011/0216179 A1 | 9/2011 | Dialameh et al. |
| 2011/0221656 A1 | 9/2011 | Haddick et al. |
| 2011/0221657 A1 | 9/2011 | Haddick et al. |
| 2011/0221658 A1 | 9/2011 | Haddick et al. |
| 2011/0221659 A1 | 9/2011 | King, III et al. |
| 2011/0221668 A1 | 9/2011 | Haddick et al. |
| 2011/0221669 A1 | 9/2011 | Shams et al. |
| 2011/0221670 A1 | 9/2011 | King, III et al. |
| 2011/0221671 A1 | 9/2011 | King, III et al. |
| 2011/0221672 A1 | 9/2011 | Osterhout et al. |
| 2011/0221793 A1 | 9/2011 | King, III |
| 2011/0221896 A1 | 9/2011 | Haddick et al. |
| 2011/0221897 A1 | 9/2011 | Haddick et al. |
| 2011/0222735 A1 | 9/2011 | Imai et al. |
| 2011/0222745 A1 | 9/2011 | Osterhout et al. |
| 2011/0224967 A1 | 9/2011 | Van Schaik |
| 2011/0225536 A1 | 9/2011 | Shams et al. |
| 2011/0229023 A1 | 9/2011 | Jones et al. |
| 2011/0231757 A1 | 9/2011 | Haddick et al. |
| 2011/0267490 A1 | 11/2011 | Göktekin et al. |
| 2011/0279222 A1 | 11/2011 | LeGree |
| 2011/0292204 A1 | 12/2011 | Boncyk et al. |
| 2011/0295742 A1 | 12/2011 | Boncyk et al. |
| 2011/0298723 A1 | 12/2011 | Fleizach et al. |
| 2011/0298939 A1 | 12/2011 | Melikian |
| 2012/0001932 A1 | 1/2012 | Burnett et al. |
| 2012/0002872 A1 | 1/2012 | Boncyk et al. |
| 2012/0028577 A1 | 2/2012 | Rodriguez et al. |
| 2012/0029920 A1 | 2/2012 | Kurzweil et al. |
| 2012/0044338 A1 | 2/2012 | Lee et al. |
| 2012/0046947 A1 | 2/2012 | Fleizach |
| 2012/0053826 A1 | 3/2012 | Slamka |
| 2012/0054796 A1 | 3/2012 | Gagnon et al. |
| 2012/0062357 A1 | 3/2012 | Slamka |
| 2012/0062445 A1 | 3/2012 | Haddick et al. |
| 2012/0075168 A1 | 3/2012 | Osterhout et al. |
| 2012/0080523 A1 | 4/2012 | D'urso et al. |
| 2012/0081282 A1 | 4/2012 | Chin |
| 2012/0092460 A1 | 4/2012 | Mahoney |
| 2012/0098764 A1 | 4/2012 | Asad et al. |
| 2012/0113019 A1 | 5/2012 | Anderson |
| 2012/0119978 A1 | 5/2012 | Border et al. |
| 2012/0120103 A1 | 5/2012 | Border et al. |
| 2012/0143495 A1 | 6/2012 | Dantu |
| 2012/0147163 A1 | 6/2012 | Kaminsky |
| 2012/0154144 A1 | 6/2012 | Betts et al. |
| 2012/0154561 A1 | 6/2012 | Chari |
| 2012/0163667 A1 | 6/2012 | Boncyk et al. |
| 2012/0163722 A1 | 6/2012 | Boncyk et al. |
| 2012/0179468 A1 | 7/2012 | Nestares |
| 2012/0183941 A1 | 7/2012 | Steinmetz |
| 2012/0194418 A1 | 8/2012 | Osterhout et al. |
| 2012/0194419 A1 | 8/2012 | Osterhout et al. |
| 2012/0194420 A1 | 8/2012 | Osterhout et al. |
| 2012/0194549 A1 | 8/2012 | Osterhout et al. |
| 2012/0194550 A1 | 8/2012 | Osterhout et al. |
| 2012/0194551 A1 | 8/2012 | Osterhout et al. |
| 2012/0194552 A1 | 8/2012 | Osterhout et al. |
| 2012/0194553 A1 | 8/2012 | Osterhout et al. |
| 2012/0195467 A1 | 8/2012 | Boncyk et al. |
| 2012/0195468 A1 | 8/2012 | Boncyk et al. |
| 2012/0200488 A1 | 8/2012 | Osterhout et al. |
| 2012/0200499 A1 | 8/2012 | Osterhout et al. |
| 2012/0200595 A1 | 8/2012 | Lewis et al. |
| 2012/0200601 A1 | 8/2012 | Osterhout et al. |
| 2012/0200724 A1 | 8/2012 | Dua et al. |
| 2012/0206322 A1 | 8/2012 | Osterhout et al. |
| 2012/0206323 A1 | 8/2012 | Osterhout et al. |
| 2012/0206334 A1 | 8/2012 | Osterhout et al. |
| 2012/0206335 A1 | 8/2012 | Osterhout et al. |
| 2012/0206485 A1 | 8/2012 | Osterhout et al. |
| 2012/0212398 A1 | 8/2012 | Border et al. |
| 2012/0212399 A1 | 8/2012 | Border et al. |
| 2012/0212400 A1 | 8/2012 | Border et al. |
| 2012/0212406 A1 | 8/2012 | Osterhout et al. |
| 2012/0212414 A1 | 8/2012 | Osterhout et al. |
| 2012/0212484 A1 | 8/2012 | Haddick et al. |
| 2012/0212499 A1 | 8/2012 | Haddick et al. |
| 2012/0218172 A1 | 8/2012 | Border et al. |
| 2012/0218301 A1 | 8/2012 | Miller |
| 2012/0227812 A1 | 9/2012 | Quinn et al. |
| 2012/0227813 A1 | 9/2012 | Meek et al. |
| 2012/0227820 A1 | 9/2012 | Poster |
| 2012/0235883 A1 | 9/2012 | Border et al. |
| 2012/0235884 A1 | 9/2012 | Miller et al. |
| 2012/0235885 A1 | 9/2012 | Miller et al. |
| 2012/0235886 A1 | 9/2012 | Border et al. |
| 2012/0235887 A1 | 9/2012 | Border et al. |
| 2012/0235900 A1 | 9/2012 | Border et al. |
| 2012/0236030 A1 | 9/2012 | Border et al. |
| 2012/0236031 A1 | 9/2012 | Haddick et al. |
| 2012/0242678 A1 | 9/2012 | Border et al. |
| 2012/0242697 A1 | 9/2012 | Border et al. |
| 2012/0242698 A1 | 9/2012 | Haddick et al. |
| 2012/0249797 A1 | 10/2012 | Haddick et al. |
| 2014/0303687 A1 | 10/2014 | Wall, III |

FOREIGN PATENT DOCUMENTS

| | | | | |
|---|---|---|---|---|
| CN | 101791259 | | 8/2010 | |
| DE | 102008059175 | | 5/2010 | |
| DE | 102009059820 | | 6/2011 | |
| EP | 2065871 | | 6/2009 | |
| EP | 2096614 | | 9/2009 | |
| EP | 2371339 | * | 5/2011 | ............... A61H 3/06 |
| EP | 2371339 | | 10/2011 | |
| EP | 2395495 | | 12/2011 | |
| JP | 2002- 219142 | | 8/2002 | |
| KR | 10-2003-0015936 | | 2/2003 | |
| KR | 10-2006-0071507 | | 6/2006 | |
| WO | WO 97/017043 | | 5/1997 | |
| WO | WO 97/018523 | | 5/1997 | |
| WO | WO 1998/032044 | | 7/1998 | |
| WO | WO 1998/036793 | | 8/1998 | |
| WO | WO 1998/036795 | | 8/1998 | |
| WO | WO 1998/036796 | | 8/1998 | |
| WO | WO 1998/037691 | | 8/1998 | |
| WO | WO 1998/055833 | | 12/1998 | |
| WO | WO 2001/003635 | | 1/2001 | |
| WO | WO 2002/089053 | | 11/2002 | |
| WO | WO 2003/078929 | | 9/2003 | |
| WO | WO 2003/107039 | | 12/2003 | |
| WO | WO 2006/083508 | | 8/2006 | |
| WO | WO 2006/085310 | | 8/2006 | |
| WO | WO 2007/063360 | | 6/2007 | |
| WO | WO 2007/095621 | | 8/2007 | |
| WO | WO 2007/138378 | | 12/2007 | |
| WO | WO 2008/020362 | | 2/2008 | |
| WO | WO 2008/052166 | | 5/2008 | |
| WO | WO 2008/109781 | | 9/2008 | |
| WO | WO 2008/116288 | | 10/2008 | |
| WO | WO 2009/154438 | | 12/2009 | |
| WO | WO 2010/145013 | | 1/2010 | |
| WO | WO 2010/142689 | | 12/2010 | |
| WO | WO 2011/017653 | | 2/2011 | |
| WO | WO 2013/067513 | | 5/2013 | |

OTHER PUBLICATIONS

International Search Report and Written Opinion in International Application No. PCT/US2012/063577, dated Feb. 20, 2013, 12 pages.

(56) References Cited

OTHER PUBLICATIONS

International Preliminary Report on Patentability in International Application No. PCT/US2012/063577, dated May 15, 2014, 8 pages.
International Search Report and Written Opinion in International Application No. PCT/US2012/063619, dated Mar. 29, 2013, 14 pages.
International Preliminary Report on Patentability in International Application No. PCT/US2012/063619, dated May 15, 2014, 9 pages.
Adjouadi, "A man-machine vision interface for sensing the environment," *J Rehabilitation Res.* 29(2): 57-76 (1992).
Censi et al., "Image Stabilization by Features Trading," IEEE International Conference on Image Analysis and Processing, 1999, pp. 665-667.
Chang et al., "Digital image translational and rotational motion stabilization using optimal flow technique," *IEEE Transactions on Consumer Electronics* 48(1): 108-115 (2002).
Chen et al., "Video Stabilization Using a Block-Based Parametric Motion Model," *Stanford University Department of Electrical Engineering Technical Report*, 2000, 32 pages.
Crawford, "Living Without a Balancing Mechanism," *Brit. J. Ophthal.* 48: 357-360 (1964).
Drahansky et al., "Accelerometer Based Digital Video Stabilization for General Security Surveillance Systems," *Int. J. of Security and Its Applications*, 4(1): 1-10 (2010).
Grossman et al., "Frequency and velocity of rotational head perturbations during locomotion," *Exp. Brain Res.* 70: 470-476 (1988).
Grossman et al., "Performance of the Human Vestibuloocular Reflex During Locomotion," *J. Neurophys.* 62(1): 264-272 (1989).
Grossman and Leigh, "Instability of Gaze during Locomotion in Patients with Deficient Vestibular Function," *Ann. Neurol.* 27(5): 528-532 (1990).
Hirasaki et al., "Effects of walking velocity on vertical head and body movements during locomotion," *Exp. Brain Research* 127: 117-130 (1999).
Horn et al., "Time to contact relative to a planar surface," *IEEE Intelligent Vehicles Symposium* 1-3: 45-51 (2007), Oct. 11, 2016.
Horn et al., "Hierarchical framework for direct gradient-based time-to-contact estimation," *IEEE Intelligent Vehicles Symposium* 1-2: 1394-1400 (2009).
Itti et al., "Computational modelling of visual attention," *Nat. Rev. Neurosci.* 2(3): 194-203 (2001).
Karacs et al., "Bionic Eyeglass: an Audio Guide for Visually Impaired," *IEEE Biomedical Circuits and Systems Conference*, 2006, pp. 190-193.
Quattoni et al., "Recognizing Indoor Scenes," *IEEE Conference on Computer Vision and Pattern Recognition*, 2009, pp. 413-420.
Roska et al., "System aspects of a bionic eyeglass," *Proceedings of the IEEE International Symposium on Circuits and Systems*, 2006, pp. 164-167.
Sachs et al., "Image Stabilization Technology Overview," 2011, downloaded from internet address http://www.invensense.com/mems/gyro/documents/whitepapers/ImageStabilizationWhitepaper_051606.pdf, 18 pages.
Turk et al., "Eigenfaces for Recognition," *J. Cognitive Neuroscience* 31(3): 71-86 (1991).
Unknown, "Augmented Reality for the Totally Blind," 2011, downloaded from internet address http://www.seeingwithsound.com, 1 page.
Unknown, "LiDAR Glasses for Blind People," 2011, downloaded from internet address http://blog.lidarnews.com/lidar-glasses-for-blind-people, 1 page.
Uomori et al., "Automatic image stabilizing system by full-digital signal processing," *IEEE Transactions on Consumer Electronics* 36(3): 510-519 (1990).
Viola et al., "Rapid Object Detection using a Boosted Cascade of Simple Features," *IEEE Conference on Computer Vision and Pattern Recognition*, 2001, pp. 511-518.
Wagner et al., "Color Processing in Wearable Bionic Eyeglass," *Proceedings of the 10th IEEE International Workshop on Cellular Neural Networks and Their Applications*, 2006, pp. 1-6.
Xiao et al., "SUN Database: Large Scale Scene Recognition from Abbey to Zoo," *IEEE Conference on Computer Vision and Pattern Recognition*, 2010, pp. 3485-3492.
Zijlstra et al., "Assessment of spatio-temporal gait parameters from trunk accelerations during human walking," *Gait & Posture* 18: 1-10 (2003).
Zöllner et al., "NAVI—Navigational Aids for the Visually Impaired," 2011, downloaded from internet address http://hci.uni-konstanz.de/blog/2011/03/15/navi/?lang=en, 2 pages.
CN Office Action in Chinese Appln. No. 201710998905.6, dated Aug. 20, 2019, 30 pages (with English translation).

\* cited by examiner

ADAPTIVE VISUAL ASSISTIVE DEVICE

CROSS-REFERENCE TO RELATED APPLICATIONS

This application is a national stage application under 35 U.S.C. § 371 of PCT Patent Application No. PCT/US2012/063619, filed on Nov. 5, 2012, which claims priority under 35 U.S.C. § 119 to U.S. Provisional Application Nos. 61/555,930 and 61/555,908, each filed on Nov. 4, 2011, the entire contents of each of which are incorporated herein by reference.

STATEMENT AS TO FEDERALLY SPONSORED RESEARCH

This invention was made with Government support under Veterans Administration Center grant number C4266C. The Government has certain rights in this invention.

TECHNICAL FIELD

This disclosure relates to wearable assistive devices that provide information to the user, such as prostheses to assist patients with visual impairment.

BACKGROUND

Visual impairment is a debilitating, life-altering condition that is difficult to overcome. The complexity of vision as a sensation and the complex neural interactions between the eyes and brain make it challenging to construct artificial devices that aim to replace lost or impaired vision in visually impaired persons. In addition, for patients, learning to interpret information from sensory augmentation devices can prove to be a significant obstacle.

SUMMARY

The methods and systems disclosed herein provide sensory information to persons, including those who suffer from visual impairment. The systems are typically implemented as a wearable visual assistive device, such as a prosthesis housed in an eyeglass frame, with a variety of additional integrated components that measure and transmit information to the user. In addition, the systems can optionally include or be used in conjunction with one or more implantable receivers (such as ocular implants, for example) that can be used to deliver additional sensory information to the user. The systems can also be implemented as visual assistive devices for users who are not visually impaired. Such devices can function as sensory augmentation devices, for example.

Rather than detecting and conveying a large quantity of sensory information to the user, which can be both computationally prohibitive for a portable system and difficult for a human being to properly interpret, the methods and systems disclosed herein are capable of adaptively detecting and processing acquired sensory information according to the environment in which the assistive device is used and the type of activity in which the user is engaged. By adaptively adjusting their behavior, the systems and methods can use relatively modest hardware (which is sufficiently portable so that it does not overly burden the user), and can selectively deliver only the most relevant information to the user. By specifically tailoring the detection and transmission of information to the environment and to the user's activities, confusion of the user is reduced, the ability of the user to adapt his or her senses to use of the assistive device is improved, the bulkiness of the hardware worn by the user is reduced, and the processing time for delivery of information to the user is reduced to a level such that the assistive device allows the user to perform activities of everyday living, like walking in an unfamiliar environment, based on information that is received in a timely fashion from the assistive device.

In general, in a first aspect, the disclosure features a visual assistive device that includes a detection apparatus configured to receive information about an environment surrounding a user of the visual assistive device, a communication apparatus configured to transmit information to the user, and an electronic processor coupled to the detection apparatus and the communication apparatus, and configured to: receive information about an activity of the user; filter the information about the environment surrounding the user based on the activity of the user; assign a priority rank to each element of the filtered information based on the activity of the user; and transmit at least some of the elements of the filtered information, according to the assigned priority ranks, to the user using the communication apparatus.

Embodiments of the device can include one or more of the following features.

The detection apparatus can include at least one image detector configured to obtain images of the environment surrounding the user. The detection apparatus can include at least one microphone. The detection apparatus can include at least one global positioning system (GPS) sensor. The detection apparatus can include at least one of a range-finding sensor and an acoustic wave sensor. The detection apparatus can include at least one motion sensor.

The device can include a housing for the detection apparatus configured to be worn on a head of the user. The housing can include the electronic processor. The housing can be configured to be worn on a portion of the user's body other than the head.

The detection apparatus and the electronic processor can be coupled through a wireless communication interface. The communication apparatus and the electronic processor can be coupled through a wireless communication interface.

The communication interface can include at least one speaker configured to transmit information to the user, and the transmitted information can include audio information derived from information received by the detection apparatus, and transmitted to the speaker by the electronic processor. The communication interface can include at least one vibrotactile transmitter configured to contact skin of the user's body, and the electronic processor can be configured to transmit information to the user based on the information received by the detection apparatus, the transmitted information including vibrotactile signals applied to the skin of the user's body.

The device can include a wireless communication interface, where the electronic processor is coupled through the wireless communication interface to an implanted prosthetic device in the user's body and configured to transmit information to the implanted prosthetic device using the wireless communication interface. The transmitted information can include visual information derived from the information received by the detection apparatus.

The electronic processor can be configured to receive information about the activity of the user by processing at least one of an audio command and a non-verbal command issued by the user and received by the detection apparatus. The electronic processor can be configured to receive information about the activity of the user by processing at least one of visual, audio, distance, gesture, and textual information received by the detection apparatus. The electronic processor can be configured to receive information about the activity of the user by processing position information received by the detection apparatus.

Prior to assigning the priority ranks, the electronic processor can be configured to identify one, a plurality, or all of the elements of the filtered information. The elements can include one or more objects in visual information received by the detection apparatus. The elements can include one or more faces in visual information received by the detection apparatus. The elements can include a position of the user in positioning information received by the detection apparatus. The elements can include one or more portions of text in visual information received by the detection apparatus.

Prior to transmitting the at least some elements of the filtered information to the user, the electronic processor can be configured to further process the at least some elements of the filtered information to refine the at least some elements. Refining the at least some elements includes assigning an identity to elements that correspond to faces in visual information received by the detection apparatus. Alternatively, or in addition, refining the at least some elements includes assigning an identity to elements that correspond to objects in visual information received by the detection apparatus. Alternatively, or in addition, refining the at least some elements includes assigning an identity to a speaker of elements that correspond to speech in audio information received by the detection apparatus. Alternatively, or in addition, refining the at least some elements includes identifying a color associated with elements that correspond to objects in visual information received by the detection apparatus.

The electronic processor can be configured to filter the information about the environment surrounding the user by determining that the activity of the user includes at least one task associated with everyday living. The electronic processor can be configured to filter the information about the environment surrounding the user by applying one or more threshold conditions associated with the activity of the user. The electronic processor can be configured to assign a priority rank to each element of the filtered information by assigning a first or highest priority rank to elements of the filtered information that correspond to hazards in the environment surrounding the user. The electronic processor can be configured to assign a priority rank lower than first to elements of the filtered information that correspond to signs, buildings, landmarks, location signals from embedded radiofrequency tags, and navigational instructions.

The activity of the user can be reading, and the electronic processor can be configured to assign a highest priority rank to elements of the filtered information that correspond to headlines and titles, and a lower priority rank to elements of the filtered information that correspond to other text.

The electronic processor can be configured to assign the priority rank to each element corresponding to an object in visual information received by the detection apparatus based on at least one of a distance between the object and the user, and an angular relationship between the object and either a direction in which the user is oriented, or a direction in which the user is gazing.

The electronic processor can be configured to refine the elements of the filtered information by transmitting the elements to a remote electronic processor, and receiving information corresponding to the refined elements from the remote electronic processor. The remote electronic processor can include a remote computer system.

The housing can include frames configured to support eyeglass lenses.

Prior to transmitting the at least some elements of the filtered information, the electronic processor can be configured to re-assess the priority ranks of one or more elements of the filtered information, and transmit the one or more elements of the filtered information according to the re-assessed priority ranks. The electronic processor can be configured to determine whether a triggering event for re-assessment of the priority ranks has occurred prior to transmitting the at least some elements of the filtered information, and re-assess the priority ranks only if a triggering event has occurred. The electronic processor can be configured to re-assess the priority ranks by retrieving a set of rules from a database based on the activity of the user, and applying the set of rules to the one or more elements of the filtered information.

The detection apparatus can be configured to receive additional information about the environment surrounding the user, and the electronic processor can be configured to adjust a configuration of the detection apparatus prior to the apparatus receiving the additional information. The electronic processor can be configured to determine components of motion of the user in visual information received by the detection apparatus, and adjust the configuration of the detection apparatus to compensate for at least some of the components of motion. The at least some of the components of motion can correspond to involuntary motion of the user.

The communication interface can include a pair of vibrotactile transmitters positioned on opposite sides of the device, where the pair of transmitters are configured to transmit navigation information to the user, and at least one additional vibrotactile transmitter, where the at least one additional vibrotactile transmitter is configured to transmit another type of information to the user different from navigation information. The pair of vibrotactile transmitters can be configured to apply vibrotactile signals to the skin of the user's body at a first frequency, and the at least one additional vibrotactile transmitter can be configured to apply vibrotactile signals to the skin of the user's body at a second frequency different from the first frequency. The pair of vibrotactile transmitters can be configured to apply vibrotactile signals to the skin of the user's body at a first signal amplitude, and the at least one additional vibrotactile transmitter can be configured to apply vibrotactile signals to the skin of the user's body at a second signal amplitude different from the first signal amplitude.

The communication interface can include at least one display configured to transmit information to the user, and the transmitted information can include visual information derived from information received by the detection apparatus, and transmitted to the display by the electronic processor. The housing can be configured to support eyeglass lenses, and the at least one display can be positioned at a location on the housing that corresponds to a location of the eyeglass lenses.

The at least one element of the filtered information can correspond to text in the environment surrounding the user, and the electronic processor can be configured to assign a priority rank to the at least one element corresponding to text based on a distance between the user and the text.

The electronic processor can be configured to determine an identity of the user.

A visual assistive system can include the visual assistive device, and a visual prosthetic device, embedded: in, or in proximity to, an eye of the user; or in, or in proximity to, an optic nerve of the user; or within, along, or in proximity to a visual pathway or visual region of a brain of the user. The electronic processor can be configured to transmit at least some of the elements of the filtered radiation derived from visual information received by the detection apparatus to the visual prosthetic device, and the visual prosthetic device can be configured to transmit a representation of each of the transmitted elements to at least one of the eye of the user, the optic nerve of the user, and the visual pathway or visual region of the brain of the user.

Embodiments of the device and the system can also include any of the other features disclosed herein, in any combination, as appropriate.

In another aspect, the disclosure features a method for providing environmental information to a visually impaired subject, the method including receiving information about an environment surrounding the subject, determining an activity of the subject, filtering the information about the environment surrounding the subject based on the subject's activity, assigning a priority rank to each element of the filtered information based on the subject's activity, and transmitting at least some of the elements of the filtered information, according to the assigned priority ranks, to the subject.

Embodiments of the method can include any one or more of the following features.

Filtering the information about the environment surrounding the subject based on the subject's activity can include filtering the information based on one or more threshold conditions associated with the activity of the subject. The information about the environment surrounding the subject can include one or more of visual information about the environment, audio information about the environment, motion information about the subject, motion information about the environment, position information about the subject, position information about one or more objects in the environment, an ambient light intensity of the environment, information indicating whether the subject is indoors or outdoors, and information about distances between objects and the subject in the environment.

Transmitting the at least some elements of the filtered information to the subject can include transmitting the at least some elements to a communications interface, and using the communications interface to transmit the at least some elements to the subject. The at least some elements of the filtered information can be transmitted wirelessly to the communications interface.

Determining an activity of the subject can include processing at least one of an audio command issued by the subject and a non-verbal command issued by the subject. Determining an activity of the subject can include processing at least one of visual, audio, position, distance, gesture, and textual information about the environment surrounding the subject.

The method can include, prior to assigning the priority ranks, identifying one or more of the elements of the filtered radiation. Identifying each of the elements of the filtered radiation can include at least one of locating objects in visual information about the environment surrounding the subject, locating faces in visual information about the environment surrounding the subject, determining a position of the subject relative to the environment surrounding the subject, and locating portions of text in the visual information about the environment surrounding the subject.

The method can include, prior to transmitting the at least some elements of the filtered information to the subject, further processing the at least some elements of the filtered information to refine the at least some elements. Refining the at least some elements can include at least one of assigning an identity to elements that correspond to faces in visual information about the environment surrounding the subject, assigning an identity to elements that correspond to objects in visual information about the environment surrounding the subject, assigning an identity to a speaker of elements that correspond to speech in audio information about the environment surrounding the subject, and identifying a color associated with elements that correspond to objects in visual information about the environment surrounding the subject.

The activity of the subject can include at least one task of everyday living. Assigning a priority rank to each element of the filtered information can include assigning a first or highest priority rank to elements of the filtered information that correspond to hazards in the environment surrounding the subject. The method can include assigning a priority rank lower than first to elements of the filtered information that correspond to signs, buildings, landmarks, location signals from embedded radiofrequency tags, and navigational instructions.

The method can include, for each element corresponding to an object in the environment surrounding the subject, assigning the element's priority rank based on at least one of a distance between the object and the subject, and an angular relationship between the object and either a direction in which the subject is oriented or a direction of the subject's gaze.

Refining the elements of the filtered radiation can include transmitting the elements to a remote electronic processor, and receiving information corresponding to the refined elements from the remote electronic processor.

The method can include, prior to transmitting the at least some elements of the filtered information, re-assessing the priority ranks of one or more elements of the filtered information, and transmitting the one or more elements of the filtered radiation according to the re-assessed priority ranks. The method can include determining whether a triggering event for re-assessment of the priority ranks has occurred prior to transmitting the at least some elements of the filtered information, and re-assessing the priority ranks only if a triggering event has occurred. The method can include re-assessing the priority ranks by retrieving a set of rules from a database based on the activity of the subject, and applying the set of rules to the one or more elements of the filtered information.

The method can include receiving additional information about the environment surrounding the subject, and prior to receiving the additional information, adjusting a configuration of a detection apparatus used to receive the additional information. The method can include determining components of motion of the user in the information about the environment surrounding the subject, and adjusting the configuration of the detection apparatus to compensate for at least some of the components of motion. The at least some of the components of motion can correspond to involuntary motion of the user.

At least one element of the filtered information can correspond to text in the environment surrounding the subject, and the method can include assigning a priority rank to the at least one element corresponding to text based on a distance between the subject and the text.

The method can include determining an identity of the subject.

Embodiments of the methods can also include any of the other features or steps disclosed herein, in any combination, as appropriate.

In addition, embodiments of the devices, systems, and methods can also include any one or more of the following features, in any combination, as appropriate.

The device can be an adaptive device. The electronic processor can be configured to receive one or more images from the detection apparatus and operating information about the device from a sensor. The electronic processor can determine, based upon the one or more images and the operating information, an activity of the user. The electronic processor can adjust a configuration of the detection apparatus based on the activity of the user, and/or process one or more images from the adjusted detection apparatus based on the activity of the user.

The electronic processor can deliver information derived from processing the images to the user wearing the device based on the activity of the user. The electronic processor can be configured to transfer the one or more images and operating information about the device to a remote electronic processor, and the electronic processor can be configured to receive information that includes a determination of the activity of the user from the remote electronic processor. The electronic processor can be configured to transfer the one or more images from the adjusted detection apparatus to a remote electronic processor where they are processed, and the electronic processor can be configured to receive information derived from the processing by the remote electronic processor. Images can be transmitted wirelessly between the electronic processor and the remote electronic processor.

The sensor can include an audio detector and/or a motion detector and/or a detector configured to receive at least one of electromagnetic and acoustic signals. The sensor can include one or more switches that can be activated by the user. The detection apparatus can include an image sensing element selected from the group consisting of a charge-coupled device (CCD) sensor, a complementary metal oxide semi-conductor (CMOS)-based sensor, and an array of diodes. The detection apparatus can include at least two image sensing elements.

At least a first portion of the detection apparatus and the sensor can be attached to a support structure, where the support structure is configured to be worn on a head of the person wearing the device. The support structure can include eyeglass frames. The electronic processor may not be attached to the support structure, and the electronic processor can be in wireless communication with the detection apparatus and the sensor. The electronic processor can be attached to the support structure, and the electronic processor can be connected to the detection apparatus and the sensor through a communication line.

The device can include a transmitting apparatus configured to receive information from the electronic processor derived from the processed images, and configured to transmit the received information to the user. The transmitting apparatus can include at least two of an audio signal transmitter, an electromagnetic signal transmitter, and a vibrotactile signal transmitter. The transmitting apparatus can include a first transmitter and a second transmitter, and the first and second transmitters can be configured to transmit different information to the user. The first transmitter can be configured to transmit information about hazards in the vicinity of the user, and the second transmitter can be configured to transmit navigational information to the user. The transmitting apparatus can include an implantable ocular transmitter.

Information about the activity of the user can include at least one of information about the user's locomotion, information about motion of the user's head, information about motion of the user's eyes, and information about motion of the user's body. The information about the environment of the user can include at least one of information about a location of the user and information about whether the user is indoors or outdoors.

The device can include one or more sensors configured to determine information about objects within a field of view of the detection apparatus by detecting acoustic waves reflected from the objects. The electronic processor can be configured to receive one or more images from the detection apparatus and the information about the objects from the sensor, to identify regions of the one or more images that correspond to a subset of the objects, and to process the identified regions of the one or more images.

The methods can include one or more of measuring an electromagnetic or acoustic signal using a detection apparatus of an assistive device where the assistive device is worn by the user, obtaining information about an activity of the user based, for example, on an environment of the user, adjusting a configuration of the device based upon the activity of the user, measuring additional electromagnetic or acoustic signals using the detection apparatus, and processing the additional signals based upon the activity of the user, and transmitting information derived from the processed additional signals to the user. The measured electromagnetic or acoustic signal can include one or more images, one or more range finding signals, and sounds from the environment of the user.

Adjusting the configuration of the device can include determining configuration settings for the detection apparatus. The configuration settings can include at least one of a focal length of the detection apparatus, a field of view of the detection apparatus, and an orientation of the detection apparatus. Adjusting a configuration of the device can include selecting filters for use in filtering the additional electromagnetic or acoustic signals. Adjusting a configuration of the device can include selecting object detection algorithms for use in processing the additional electromagnetic or acoustic signals. The electromagnetic or acoustic signals can include one or more images, and selecting object detection algorithms can include analyzing the one or more images to identify objects in the one or more images and selecting the object detection algorithms based upon the identified objects. The object detection algorithms can include at least one of algorithms for identifying hazards, algorithms for facial recognition, and optical character recognition algorithms. Adjusting the configuration of the device based upon the activity of the user can include leaving the configuration of the device unchanged.

The additional electromagnetic or acoustic signals can include one or more images, and processing the additional signals based upon the activity of the user can include adjusting the one or more images to compensate for motion of the detection apparatus. Processing the additional signals based upon the activity of the user can include adjusting the one or more images based upon motion of the head or eyes of the user. Processing the additional signals based upon the activity of the user can include filtering the signals to remove at least a portion of the information in the signals. The additional electromagnetic or acoustic signals can include one or more images, and processing the additional signals can include identifying at least one of hazardous objects, faces of people, and printed text, in the one or more images.

The transmitted information can include at least one of audio signals, electromagnetic signals, and tactile signals. The additional electromagnetic or acoustic signals can include one or more images, and the audio signals can include warnings based upon identification of hazardous objects in the one or more images and/or identities of persons in the one or more images and/or audio transcriptions of printed text in the one or more images. The additional electromagnetic or acoustic signals can include one or more images, and processing the additional signals can include selectively identifying a subset of objects in the one or more images based upon the activity of the user, the environment of the user, or both.

The methods can include transmitting a representation of measured signals to an electronic processor remote from the device, and using the remote electronic processor to determine the activity of the user. The methods can include using an electronic processor remote from the device to adjust the configuration of the device based upon the activity of the user. The methods can include transmitting representations of the additional electromagnetic or acoustic signals to an electronic processor remote from the device, and using the remote electronic processor to process the additional signals based upon the activity of the user.

As used herein, an "activity" of a user corresponds to a particular task that a user is trying to accomplish, a goal that the user is trying to achieve, or any other user objective. Non-limiting examples of activities include navigation outdoors, navigation indoors, reading, conversing with another person, eating, and transacting business (e.g., paying with money).

As used herein, "elements" of information about a user's environment are individual features that are extracted from raw information measured by the systems disclosed herein. Non-limiting examples of elements include objects, text, speech, faces, landmarks, position information, distances, and angular orientations.

As used herein, "refining" elements of information about a user's environment corresponds to determining additional information about the elements for reporting to the user. For many such elements, after they have been located or detected in the raw information measured by the system, "refining" refers to identifying or characterizing the elements further. For example, after objects have been located, the objects are refined by identifying the objects. After text has been located, the text is refined by converting it into a series of alphanumeric characters. After speech has been detected, the speech is refined by identifying the speaker and/or the words being spoken. After faces have been located, they are refined by identifying to whom they belong. After landmarks have been located, they are refined by identifying the landmarks.

Unless otherwise defined, all technical and scientific terms used herein have the same meaning as commonly understood by one of ordinary skill in the art to which this disclosure belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments are set forth in the accompanying drawings and description below. Other features and advantages will be apparent from the description, drawings, and claims.

DESCRIPTION OF DRAWINGS

Like reference symbols in the various drawings indicate like elements.

DETAILED DESCRIPTION

I. General Introduction

Figure 1:
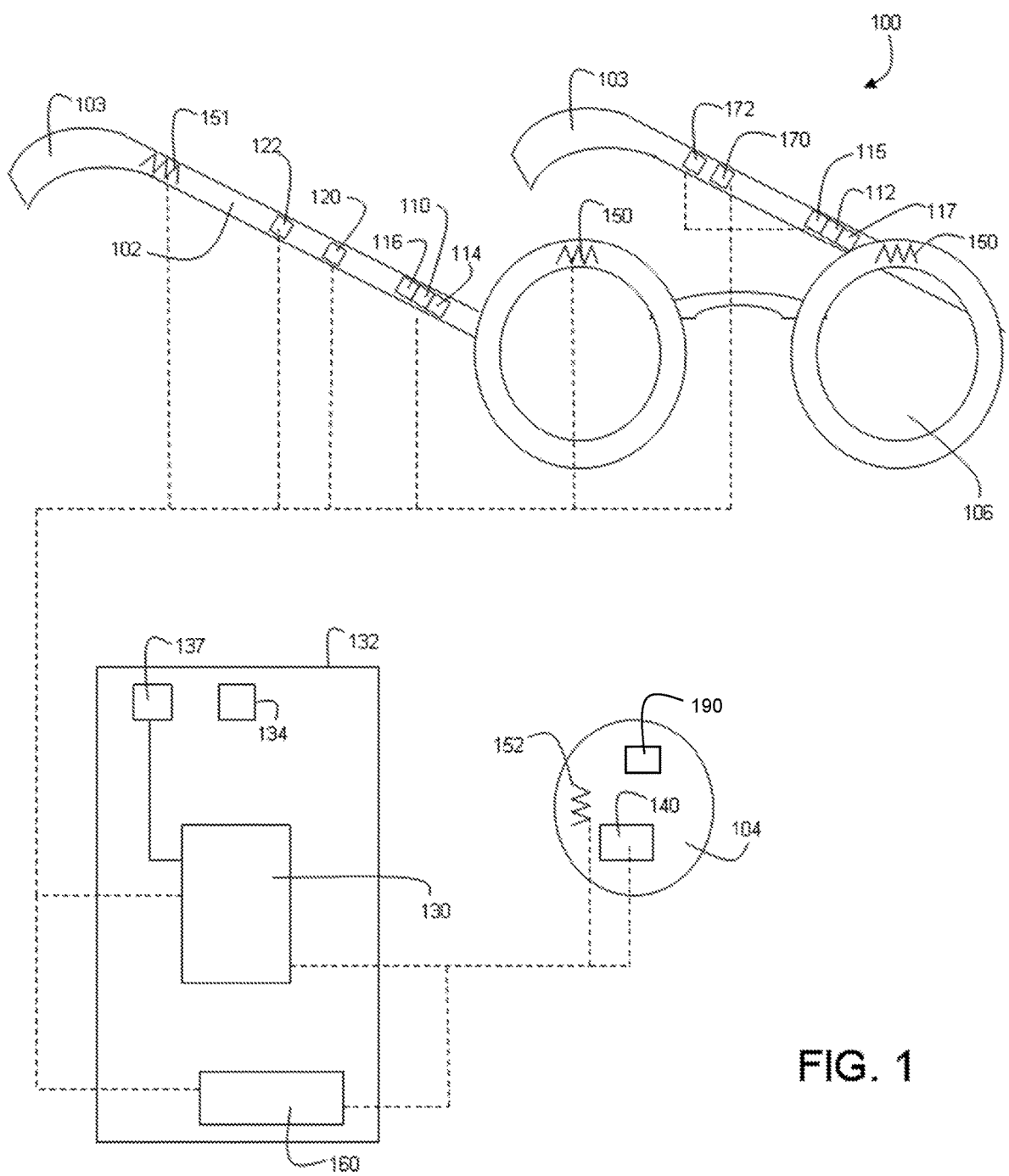
FIG. 1 is schematic diagram of an embodiment of a visual assistive device.

For individuals with visual impairment, the complex nature of the environment around them is made difficult to assess and negotiate due to their inability to make use of the sophisticated natural vision processing inherent in the human eyes and brain. To address such difficulties, conventional visual assistive devices typically adopt a common approach to providing visual information (or substituted visual information) to the user. In such assistive devices, visual information is: (a) measured and then relayed to the user; (b) measured directly by the wearable device and used to provide visual information to the user; and/or (c) processed and delivered to the user in the form of audio or tactile feedback. While such systems have certain benefits, as the amount and complexity of visual information that is acquired increases, it becomes increasingly difficult to convey the visual information to the user in a real time or near-real time (as a user is walking, for example) manner that is both helpful and not confusing. Further, measurement and processing of large volumes of information, especially in real time or near-real time, typically consumes significant energy resources and mandates relatively sophisticated computing hardware, both of which are not well suited for lightweight, wearable assistive devices. Even if only a small fraction of the available information about a person's environment were to be measured, the sheer volume of measured information would require significant computing resources to process, and it would be difficult to interpret when presented to a visually impaired person using stimuli that are non-visual in nature.

The methods and systems disclosed herein are designed to enhance the ability of a visually impaired person to negotiate his or her environment by capturing and presenting information about the environment to the person. The information presented to the person is both relevant and up-to-date in real time or near-real time. Moreover, the systems can be implemented in relatively small, portable, wearable devices such as (but not limited to) eyeglass frames. The systems include a variety of sensors, processing hardware, software instructions, and a power source, and form self-contained assistive devices. When advantageous, the systems can also communicate with a variety of external devices to obtain information about the environment and to offload computationally intensive tasks to reduce onboard hardware and power requirements.

To achieve rapid communication of relevant information to a visually impaired person, the methods and systems disclosed herein are designed to selectively process visual information (e.g., images of objects and/or faces) and/or non-visual information (e.g., audio signals such as spoken words and sounds) prior to transmission of the information to the user. In particular, by selecting only certain features from a measured image and/or by selecting only certain algorithms for processing visual and/or non-visual information, significant savings in energy consumption and computing hardware requirements are realized, which directly benefits the user. Further, by appropriate selection of detection apparatus configuration settings and processor settings, the information that is transmitted to the user can be specifically tailored to the particular circumstances of the user, thus improving the utility and ease of use of the device for the user.

As will be explained in greater detail, selectively processing information involves filtering the large volume of information collected by the multiple sensors of the systems disclosed herein according to the activity of the visually impaired person. The collected information is filtered to exclude collected information that is either irrelevant, or of low relevancy, to the person's particular activity (or set of activities). In this manner, the information that is filtered out is not processed further, reducing the computational load on the system's electronic processor.

The methods and systems disclosed herein permit measurement of multiple different types of information, including one or more images. In addition, audio, motion, range-finding, and electromagnetic signals can be measured to reflect the environment of the user of the assistive device. In addition to presenting a subset of this measured information to the user, this information can be used to adjust parameters that control operation of the system, and to control processing of the information through selection of processing and filtering algorithms that are applied to the information.

II. Visual Assistive Systems

FIG. 1 shows a schematic diagram of an embodiment of a visual assistive device 100. Assistive device 100—implemented, e.g., in part as eyeglass frames 102—includes a detection apparatus featuring detectors 110 and 112, sensors 120 and 122, receiver-transmitters 170 and 172, and an electronic processor 130 and a power source 160 positioned within an external housing 132. Actuators 114 and 116 are connected to detector 110, while actuators 115 and 117 are connected to detector 112. Although a particular arrangement of sensors 120 and 122 and receiver-transmitters 170 and 172 is shown in FIG. 1, more generally these components can be positioned in any arrangement relative to one another. For example, in some embodiments, detector 110 and/or detector 112 (and other components such as sensors 102 and/or 122) can be positioned on the bridge of eyeglass frames 102.

Actuators 114, 115, 116, and 117 can be attached to an external surface of frames 102 or embedded within frames 102 (and thus may not be directly visible, although they are depicted as visible in FIG. 1 for purposes of clarity). Although a particular arrangement of the actuators is shown in FIG. 1, more generally the actuators can be positioned at any location on the device to provide for adjustment of the position and orientation of the detectors.

One or more radiofrequency coils 150 can be attached to, or implanted within, frames 102. Further, an optional ocular implant 140 can be implanted within an eye 104 of the assistive device user, and an optional radiofrequency coil 152 can also be implanted within eye 104. Detectors 110 and 112, actuators 114 and 116, sensors 120 and 122, receiver-transmitters 170 and 172, coils 150, and implant 140 are each connected to electronic processor 130 through a wired or wireless connection. Ocular implant 140 can be implemented in a variety of ways, including as a thin film device with additional electronic components positioned within the eye or on a surface of the eye.

Although device 100 in FIG. 1 includes two detectors 110 and 112, more generally the device can include any number of detectors. In some embodiments, detectors 110 and/or 112 are configured to obtain images so that information derived from the images can be transmitted to the user of assistive device 100. In certain embodiments, detectors 110 and/or 112 are configured to measure other types of information (e.g., non-image information) that can be transmitted to the user. For example, detectors 110 and/or 112 can be range-finding detectors (e.g., laser infrared range-finding detectors and/or ultrasound-based range-finding detectors) that measure distances between assistive device 100 and objects in the user's environment.

In general, a wide variety of different detectors can be used in the device to obtain images. For example, the detectors can include CCD-based arrays, CMOS-based light sensors, diode arrays, analog video cameras, and other imaging devices. Detectors configured to obtain images can detect electromagnetic radiation in a variety of spectral regions, including the ultraviolet region, the visible region, and/or the infrared region.

Although not shown in FIG. 1, the detectors can include—in addition to one or more sensor elements—a variety of optical components that can be used to manipulate optical radiation detected by the device. Optical components that can be used in detectors include lenses, spectral filters, spatial filters, and reflective elements such as mirrors.

The assistive device shown in FIG. 1 includes two actuators 114 and 116 connected to detector 110. More generally, however, device 100 can include any number of actuators connected to any one or more detectors. In general, the actuators permit processor 130 to adjust the position and orientation of each of the detectors (via control signals sent from processor 130 to the actuators) by translating and/or rotating the detectors relative to a fixed reference point (such as the center of frames 102). In some embodiments, actuators 114 and 116 are connected to components within the detectors such as lenses, filters, and/or mirrors, permitting electronic processor to adjust the imaging properties of the detectors as well. For example, actuators 114 and 116 can be connected to an objective lens within detector 110. By translating the objective lens relative to the sensing element within detector 110, electronic processor 130 can control the focal length of detector 110. Alternatively, or in addition, actuators 114 and/or 116 can be connected to one or more lenses that can be translated to change the size of the field of view imaged by detector 110.

Assistive device 100 includes two sensors 120 and 122 in FIG. 1, although more generally, the assistive device can include any number of sensors. Many different types of sensors can be used to provide a wide variety of information to processor 130. In some embodiments, for example, assistive device 100 can include one or more motion sensors that provide information about translational and/or rotational motion of assistive device 100 (and, therefore, the head of the user of assistive device 100) to processor 130. Suitable motion sensors include accelerometers, gyroscopes, and magnetometers, for example.

In general, sensors 120 and 122 can be positioned at any location on the assistive device. In FIG. 1, sensors 120 and 122 are positioned on an arm of the eyeglass frames. Sensors in other positions can also be used, however. For example, a first group of sensors can be positioned in the assistive device (e.g., in the eyeglass frames shown in FIG. 1), and a second group of sensors can be positioned in external housing 132 to provide a reference to which measurements by the first group of sensors can be related.

In some embodiments, assistive device 100 can include one or more audio detectors such as microphones. The one or more audio detectors can be configured to detect a wide variety of sounds in the environment surrounding assistive device 100, to convert the detected sounds into electronic signals, and to transmit the electronic signals to processor 130. In certain embodiments, the detected sounds include audible commands issued by the user of assistive device 100. These audible commands are processed by voice recognition algorithms executed by processor 130, and used to determine an activity of the user of assistive device 100 (as discussed in more detail later). Based on the activity of the user, device 100 can then convey a subset of the information about the user's environment to the user to assist the user's activity. For example, if the user of assistive device 100 is engaged in navigation, audio sensors in the assistive device can detect warning sounds such as vehicle horns and sirens, processor 130 can extract and interpret these sounds from the measured audio signals, and the device can convey some or all of this information to the user to allow him or her to avoid hazards represented by the sounds.

Further, in some embodiments, audio information can be transmitted to, and interpreted by, a remote person monitoring assistive device 100. The remote person can then transmit information, including verbal, textual, and/or vibrotactile signals, to the user of the assistive device to assist the user's activity.

In certain embodiments, assistive device 100 can include one or more sensors configured to receive electromagnetic signals. A wide variety of signals can be received and appropriate information transmitted to processor 130. For example, assistive device 100 can include one or more GPS receivers configured to receive GPS positioning information from a remote server or a remote GPS satellite. The position information is transmitted to processor 130 and used to determine a location of assistive device 100.

In some embodiments, assistive device 100 can include one or more sensors for receiving radiofrequency signals. The radiofrequency signals can be terrestrial radiofrequency signals broadcast by transmitters and providing positioning information (e.g., the signals can be used by processor 130 to determine a location of assistive device 100 using methods such as distance estimation and triangulation). In certain embodiments, the radiofrequency signals can be signals from radiofrequency identification (RFID) tags embedded in structures such as buildings, street signs, lamp posts, objects related to tasks of everyday living, and vehicles. The RFID tag signals can be transmitted to processor 130, which can compare the signals to a database in a storage unit connected to processor 130 or stored in a remote location and accessible by processor 130, to determine information about the location of assistive device 100.

In some embodiments, assistive device 100 can include one or more sensors configured for range finding (that is, sensors that detect range finding signals). Such sensors can perform range finding by detecting a variety of electromagnetic and/or acoustic signals, including ultrasonic signals and infrared signals. Intensity and/or directional information about the detected signals can be transmitted to electronic processor 130, which can process the information to determine distances of objects in the environment of the user, and angular relationships between objects and a direction in which the user is oriented (e.g., a direction in which the user is facing, as measured by determining a direction of the user's gaze, or a direction in which the user is navigating, as determined by position information). Processing can be correlated with information extracted from images measured by other sensors (or by detectors 110 and/or 112) to correlate measured distances with specific objects.

For example, in some embodiments, assistive device 100 can include one or more sensors configured to measure image information, and one or more sensors configured to measure range-related information (e.g., by detecting ultrasonic echoes from objects in proximity to assistive device 100 and/or by detecting laser light, including infrared laser light, scattered from the objects). In this manner, assistive device 100 can estimate distances and positions of objects within the field of view of assistive device 100, and determine angular orientations of objects relative to a direction in which the user is oriented (e.g., a direction of the user's gaze and/or a direction in which the user is navigating).

This information can then be used to process other types of information such as image information accordingly. For example, if the assistive device determines that objects positioned in close proximity to the user are only located within a limited portion of the field of view of the device, processing of images obtained by the sensors can be restricted to a region of the images that corresponds to the portion of the field of view where the close objects are located. Objects that are further away within the field of view can be disregarded entirely, or processing related to such objects can be assigned to lower priority or deferred until a later time. Further, the various analysis algorithms disclosed herein can be selectively and preferentially applied to objects that are closest to the user of assistive device 100 (or which approach the user fastest), as such objects are likely to represent more immediate hazards and/or have more immediate implications for the user. Moreover, selective processing of only certain regions of images can reduce the power and processing requirements for assistive device 100, and can increase the responsiveness of the device (e.g., the rate at which information is provided to the user).

Sensor 134 (which can, in general, include one or more sensing elements) is configured to detect motion of external housing 132. In some embodiments, for example, sensor 134 includes one or more accelerometers and/or gyroscopes and/or magnetometers that provide information to processor 130 about movement of the user's body. As discussed above, processor 130 can use this information together with information about movement of the user's head to determine motion of the user's head relative to the rest of the user's body, and to adjust the configuration of the detection apparatus and to select appropriate algorithms for processing images obtained by the detection apparatus.

In some embodiments, sensor 134 includes one or more controls or switches that can be activated by the user of assistive device 100. The switches or controls provide another method (e.g., separate from issuing auditory commands) for the user to control the operation of assistive device 100. Adjustments to any of the controls by the user of the assistive device are communicated to processor 130, which can then adjust the configuration of the detection apparatus, determine the activity of the user, and/or select appropriate algorithms for processing images based on the user's adjustments.

Optional radiofrequency (RF) coils 150 can be used to detect motion of the eyes of the user of assistive device 100. For example, an ocular implant positioned in the eye(s) of the user can include one or more transmitting RF coils 152, and coils 150 mounted on frames 102 can function as receiving RF coils. When the user's eyes move, for example, the position of the ocular implant and the implanted transmitting RF coils 152 changes. As a result, the reduced RF field between the transmitting coils 152 and the receiving coils 150 changes; signals representing such changes can be measured by receiving coils 150 and transmitted to processor 130. The processor can use this information about motion of the user's eyes together with information about motion of the user's head (from sensors 120 and/or 122) and information about motion of the user's body (from sensor 134) to adjust the configuration of the detection apparatus and to select appropriate algorithms for processing images obtained by the detection apparatus. Systems and methods for detecting eye movements using RF coils are disclosed, for example, in U.S. Pat. No. 7,967,439, the entire contents of which are incorporated herein by reference.

In some embodiments, assistive device 100 can include one or more detectors (not shown in FIG. 1) mounted to the eyeglass frames and positioned to capture images of the user's eyes. In this manner, motion of the user's eyes can be detected. As described above, processor 130 can extract this information from eye images and use the information to adjust the configuration of the detection apparatus and select appropriate processing algorithms, as discussed above.

Power source 160 can generally include one or more of a variety of different portable power sources, including batteries (such as rechargeable batteries), solar cells, and kinetic energy sources either mounted on the eyeglass frames or on a portion of the user's body. Suitable kinetic energy systems are disclosed, for example, in U.S. Patent Application Publication No. US 2010/0045241, and in Y. Qi et al., "Piezoelectric Ribbons Printed onto Rubber for Flexible Energy Conversion," Nano Letters 10(2): 524-528 (2010), the entire contents of each of which are incorporated herein by reference. In some embodiments, assistive device 100 includes an optional radiofrequency coil 151 for receiving operating power from a power source located within housing 132. In certain embodiments, coil 151 can also be configured to receive visual information (e.g., images) from detectors 110 and/or 112, and can transmit this information to processor 130.

Power source 160 is configured to transmit electrical power to processor 130 and sensor 134 through either a wired or wireless connection. Power source 160 can also be configured to transmit electrical power via a wireless connection to any or all of detectors 110 and 112, sensors 120 and 122, receiver-transmitters 170 and 172, actuators 114 and 116, RF coils 150 and 152, and ocular implant 140.

Assistive device 100 includes two receiver-transmitters 170 and 172 in FIG. 1. More generally, however, assistive device 100 can include any number of receiver-transmitters, and the receiver-transmitters can be positioned anywhere on assistive device 100. For example, in some embodiments, assistive device 100 includes one or more actuators (e.g., two actuators) positioned near the ends 103 of frames 102, and one or more actuators (e.g., two actuators) positioned near the temples of frames 102.

Receiver-transmitters 170 and 172 are generally configured to receive signals transmitted by processor 130, and to transmit information to the user of assistive device 100 based on the received signals. In some embodiments, receiver-transmitters 170 and 172 are configured to transmit different types of information to the user. For example, one of the receiver-transmitters can be configured to transmit audio information to the user of assistive device 100. The audio information can include information about objects and/or people within one or more images obtained by detectors 110 and/or 112. The audio information can also include an audio representation of text appearing in the one or more images, such as printed text on a page or text printed on signs or banners. Audio information transmitted to the user can further include warnings and alerts that advise the user of potentially hazardous objects identified within the one or more images; the warnings can also advise the user if the objects are approaching the user, and can provide estimated distance and/or velocity of approach information. Audio information transmitted to the user can also include navigational information, such as the locations of upcoming streets, landmarks, buildings, and directional information (including turn-by-turn directions).

One or more of the receiver-transmitters can be configured to transmit tactile information to the user of the assistive device. For example, tactile sensations such as pressure and/or vibrations can be applied to the skin of the user (e.g., either directly or through the side bars of eyeglass frames 102) to alert the user of oncoming objects that are potentially hazardous (e.g., an applied pressure can increase or an amplitude of vibrations can increase as the object approaches). Tactile sensations can also be used to "steer" the user around obstacles and/or navigate down a street—that is, to provide navigational guidance to the user by stimulating one side or the other of the user's head to indicate that the user should move toward or away from the direction of the stimulation. Stimulation of both sides at once can carry additional significance; in some embodiments, for example, such stimulation indicates to the user that the ground ahead either rises or falls in elevation (e.g., a stairway or hazardous drop-off).

In certain embodiments, device 100 can include two or more pairs of receiver-transmitters, each configured to transmit a different type of tactile information. For example, a pair of vibrotactile receiver-transmitters, with one member of the pair positioned on each side of frames 102, can deliver navigational information to the user to steer the user during locomotion, e.g., walking. Delivery of navigational information can include, for example, varying the vibrotactile stimulation on either side of frames 102 to direct the user in the left- or right-hand directions. One or more additional vibrotactile receiver-transmitters can be positioned at a different location on frames 102 (e.g., closer to the lenses in frames 102) and can be configured to warn the user of oncoming obstacles and hazards.

To assist the user in distinguishing the vibrotactile stimulations provided by the different receiver-transmitters, in some embodiments, vibrotactile stimulations corresponding to navigational information can be delivered at a different frequency from the vibrotactile stimulations corresponding to warnings about hazards and obstacles. By delivering different types of information at different frequencies, the user can distinguish among the types of information provided by device 100 without becoming confused. Alternatively, or in addition, in certain embodiments vibrotactile stimulations corresponding to navigational information can be delivered at a different amplitude from the vibrotactile stimulations corresponding to warnings about hazards and obstacles. Further, in some embodiments, vibrotactile stimulations corresponding to navigational information can be delivered using a different mode of delivery from the vibrotactile stimulations corresponding to warnings about hazards and obstacles. For example, stimulations that correspond to navigational information can be delivered by a pair of receiver-transmitters, one on each side of frames 102, which provide biased stimulations on each side. In contrast, stimulations that correspond to navigational information can be delivered by a different pair of receiver-transmitters, one on each side of frames 102, which provide symmetrical stimulations on each side. Each of the foregoing configurations, used alone or in combination, permits device 100 to deliver more than one type of information to the user via tactile stimulation alone.

In some embodiments, tactile sensations such as pressure and/or vibrations can be used to indicate to the user that a predetermined condition has been realized (e.g., a person for whom the user is searching has been located in an image obtained by detector 110 and/or 112, or a destination toward which the user is traveling has been reached). Examples of tactile receiver-transmitters are disclosed in U.S. Patent Applications 2002/0111737, 2008/0120029, and 2001/0148607, and in U.S. Pat. Nos. 6,671,618, 7,788,032, and 7,991,576, the entire contents of each of which is incorporated herein by reference.

In certain embodiments, both audio and tactile sensory information is provided to a user of assistive device 100. For example, receiver-transmitter 170 can be configured to transmit audio information and receiver-transmitter 172 can be configured to transmit tactile information, as described above. The sensory information transmitted by each receiver-transmitter can be duplicative (e.g., both audio and tactile warnings that a hazardous object is in the vicinity of the user) to ensure that the user is aware of the information. Alternatively, in some embodiments, the information transmitted can be complementary. For example, audio information about hazardous objects or people in the images obtained by the detectors can be transmitted by one of the receiver-transmitters, and tactile information indicating to the user the approximate distance to the objects or people can be transmitted by the other receiver-transmitter. In this manner, information relevant to the user can quickly be communicated without confusing the user by transmitting information that is of less relevance.

In some embodiments, the manner in which the receiver-transmitters operate can vary according to the nature of the information that is conveyed to the user. For example, the receiver-transmitters can vibrate at relatively low frequencies to provide navigational guidance information to the user, and vibrate at notably higher frequencies to provide information about more immediate hazards in the user's vicinity. In addition, receiver-transmitters positioned at different locations on assistive device 100 can convey different types of information. For example, receiver-transmitters positioned near the temples of frames 102 can provide guidance information via low frequency and/or low amplitude vibrations, and receiver-transmitters positioned nearer to ends 103 can provide warnings and hazard information via higher frequency and/or larger amplitude vibrations.

Ocular implant 140 is generally an implantable device (e.g., implantable under or above the retina of the eye, or elsewhere within or around the eye, along the optic nerve, or along or within the visual pathways within the brain itself). Implant 140 can be an electromagnetic transceiver such as a photodiode array, for example. In some embodiments, implant 140 can be configured to receive optical radiation through lenses 106 of assistive device 100, and to convert the optical radiation to electronic signals that can be interpreted by the user of assistive device 100. In some embodiments, lenses 106 can be refractive elements configured (e.g., with appropriate curvature, focal length, and other optical properties) specifically for the eyes of the user of assistive device 100.

In certain embodiments, implant 140 can be a receiver-transmitter that receives information from processor 130 about objects, people, text, and other elements present in images obtained by detectors 110 and/or 112, converts the received information into electrical signals, and transmits the electrical signals to the user of assistive device 100 (e.g., by direct stimulation of the cortex, optic nerve, retina or another part of the user's eye). In some embodiments, an augmented reality display can be transmitted to the user. The display can include overlays (e.g., arrows, dots, and other markers) to indicate directions and highlight areas of interest.

A wide variety of different implants are suitable for use with assistive device 100. Examples of implants that can be used are described in the following U.S. Patents and Patent Applications, the contents of each of which is incorporated herein by reference: U.S. Pat. Nos. 6,976,998; 6,389,317; 6,230,057; US 2008/0288067; US 2008/0275527; US 2005/0251223; and US 2002/0111655.

Housing 132 is typically a pocket-sized enclosure for processor 130 and power source 160. In some embodiments, housing 132 can also enclose a transmitter-receiver unit 137 connected to processor 130, e.g., for transmitting and receiving information from the other components of assistive device 100. In certain embodiments, housing 132 can also enclose a storage unit (not shown in FIG. 1) connected to processor 130 for storing assistive device configuration settings, databases (e.g., databases of objects and/or faces of people, streets, interior layouts of buildings), and other information. Housing 132 can also include a plurality of ports that provide direct connections to the components within the housing; examples of ports that can be present include an electrical charging port connected to power source 160, and communication ports connected to processor 130.

In certain embodiments, housing 132 can enclose a transmitter-receiver unit (not shown in FIG. 1) connected to processor 130 and configured to transmit information to, and receive information from, remote devices and locations. Remote devices include computing devices (e.g., servers) that store databases of information as described above. More generally, the transmitter-receiver unit can provide processor 130 with a connection (wired and/or wireless) to a variety of distributed networks (e.g., a computing "cloud"). Persons and/or devices at remote locations can thereby receive information from processor 130, issue operating commands to the assistive device, and transmit information to the user of the device. A variety of transmission protocols can be used for wireless transmission of information to and from processor 130, including Bluetooth® and WiFi transmission protocols. In general, any of the processing steps disclosed herein can be performed by an electronic processor in a remote computing device that is connected to assistive device 100 via a distributed computing network. In addition, the assistive device and one or more additional electronic processors in remote computing devices connected over a distributed computing network can partition the various processing steps disclosed herein so that some or all of the steps can be executed in parallel.

A particular advantage of assistive device 100 is that the various components of device are housed within a "cosmetically acceptable" housing (e.g., eyeglass frames or a hat or cap). A barrier to adoption of assistive devices by users continues to be reluctance to wear in public devices that are unusual or strange in appearance, and/or devices where components such as cameras are visible. The devices disclosed herein can be housed within a variety of articles of clothing or other articles that are habitually worn in public such that cameras and other components of the devices are generally not visible at a distance. As such, the user of assistive device 100 does not call undue and unwanted attention to himself or herself in public when the device is worn.

In addition to eyeglass frames, housings for assistive devices can include other types of eyewear such as goggles, various articles of clothing such as hats, "hearing-aid"-style devices configured to be worn over the ear, and various types of jewelry such as necklaces, earrings, and lapel pins. In some embodiments, components of assistive device 100 can be housed in different housings and can work cooperatively; for example, certain components of device 100 such as cameras and/or sensors can be housed in earrings or a broach, while other components can be housed in a necklace that matches the earrings. In other embodiments, the device can be made in the form of, or as part of, a pair of earphones or headphones.

Figure 9:
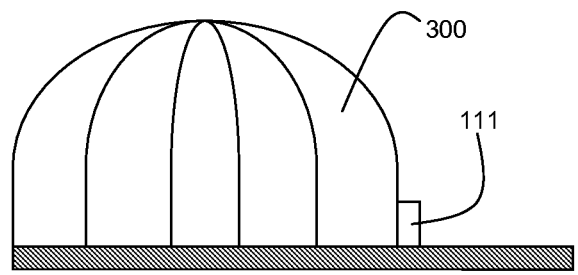
FIG. 9 is a schematic diagram of a hat with a detector for a visual assistive device.

In some embodiments, assistive device 100 can also include additional detectors attached to a different or second support structure (e.g., to a wearable structure different from eyeglass frames 102). For example, the device can include one or more detectors attached to a hat that is worn on the head of the user, or the entire device can be fitted into or onto a hat or cap in certain implementations. As another example, the device can include one or more detectors attached to a device configured to be worn over or attached to the user's ear in the style of a hearing aid. These detectors can include any of the types of detectors disclosed herein in connection with detectors 110 and 112, and can communicate information over a wired or wireless connection with processor 130, and receive electrical power wirelessly from power source 160. Processor 130 can configure each of the detectors in the detection apparatus—including detectors that are attached to the second support structure—based on information about activities in which the user is engaged and/or the environment of the user. FIG. 9 shows an embodiment of a hat 300 (e.g., a baseball cap) with a detector 111 mounted to a front surface of the hat. Detector 111 can receive operating power from power source 160, and can transmit images wirelessly to processor 130. Although depicted as a baseball cap in FIG. 9, hat 300 can be of a variety of designs. In some embodiments, for example, hat 300 is a protective helmet configured to be worn by a solider, by a fireman, or by another person engaged in hazardous activity and who benefits from receiving the information transmitted by processor 130.

III. Methods for Providing Sensory Information

The systems disclosed herein are capable of measuring a wide variety of information and, accordingly, of providing widely-varying sensory information to a user of assistive device 100. Assistive device 100 operates in general by selectively transmitting (and, in some embodiments, selectively detecting) only certain types of sensory information to the user. By reducing the amount of information that is processed by processor 130 and transmitted to the user of assistive device 100, computational time and resources can be conserved, resulting in efficient, faster, low-power operation of the assistive device. Further, sensory information derived from images obtained by the detection apparatus can be transmitted to the user in real-time, so that there is little perceived delay between information detection and transmission, and so that the user can adjust to changes in his or her dynamic environment. For purposes of this disclosure, "real-time" transmission of information to the user means that transmission of sensory information derived from a detected image occurs within 2 seconds of image detection.

Figure 2:
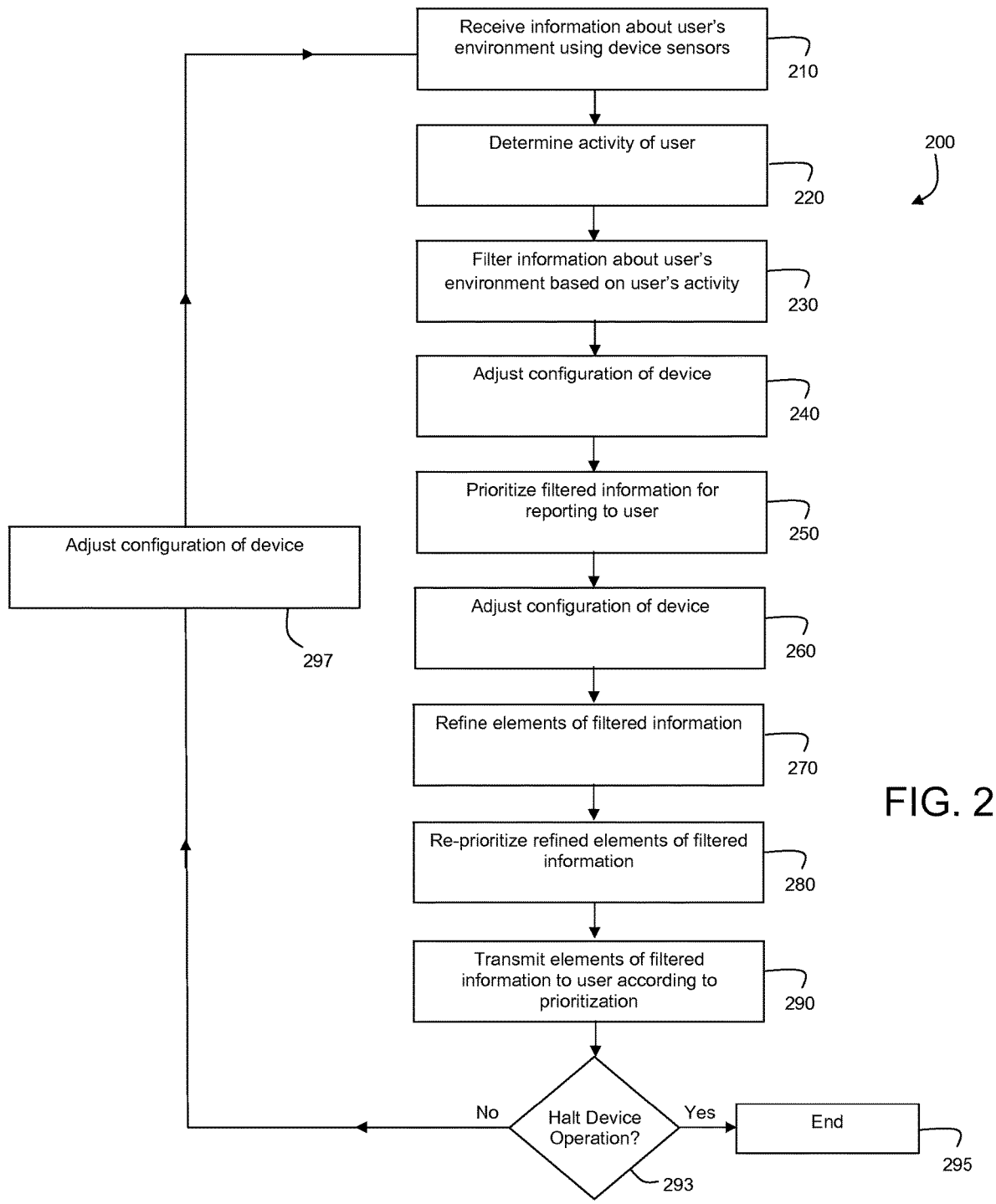
FIG. 2 is a flow chart that includes a series of steps for providing sensory information to a user of a visual assistive device.

FIG. 2 shows a flow chart 200 that includes a series of steps for providing sensory information to a user of assistive device 100. In a first step 210, information about the user's environment is received using one or more of the detectors and sensors of the device. The information is transmitted (e.g., wirelessly or via wired connections) to electronic processor 130 for further analysis.

Next, in step 220, information about the activity of the user of assistive device 100 is determined using one or more of the device's sensors. Information about the activity of the user can include signals measured by these sensors from the user, such as direct audio commands issued by the user. The information can also include information received from the environment of the user and/or measured signals from a person or computing device at a remote location. Information about the activity of the user generally includes two types or classes of information: information about the task(s) in which the user is engaged, and information about the environment of the user.

(a) Information from the User (i) Direct Commands

Information about the activity of the user of assistive device 100 can be obtained through direct commands issued by the user to the assistive device or by a remote person. Sensors 120 and/or 122 can be audio sensors that detect verbal instructions issued by the user, and transmit representations of the detected audible instructions to processor 130 for parsing. In addition, sensor 134 can include controls, e.g., in the form of switches, touchscreens, buttons, sliders, keys, or keypads, that can be activated by the user to directly transmit instructions to processor 130. In both of these examples, the instructions transmitted by the user to processor 130 involve information about various activities in which the user is engaged.

(ii) Indirect Information about the User

In addition to, or as an alternative to, explicitly issued instructions from the user, assistive device 100—through its various sensors—can also automatically measure information about activities of the user. Examples of the types of activity information that can be measured and transmitted to processor 130 follow, but the list of examples is not exhaustive, and other types of activity information can also be measured.

(1) Eye Movements

In some embodiments, movement of the user's eyes (e.g., when the user is following the motion of an object of interest) can be detected using RF coils 150, and/or using cameras mounted to frames 102, as disclosed herein. Even if the user of assistive device 100 has limited visual perception, assistive device 100 is designed so that when the user's eyes rotate in a particular direction to follow an object (either by directly perceiving the object, or by perceiving a representation of the object transmitted to the user via ocular implant 140), the change in the orientation of the user's eyes produces a change in the electromagnetic field induced in coils 150, and this change in field strength can be communicated to processor 130. Processor 130, on the basis of the change in field strength, can determine the new orientation of the user's eyes. Methods for measuring eye movements are disclosed, for example, in U.S. Pat. No. 7,967,439, the entire contents of which are incorporated herein by reference.

(2) Head and Body Movements

Figure 3:
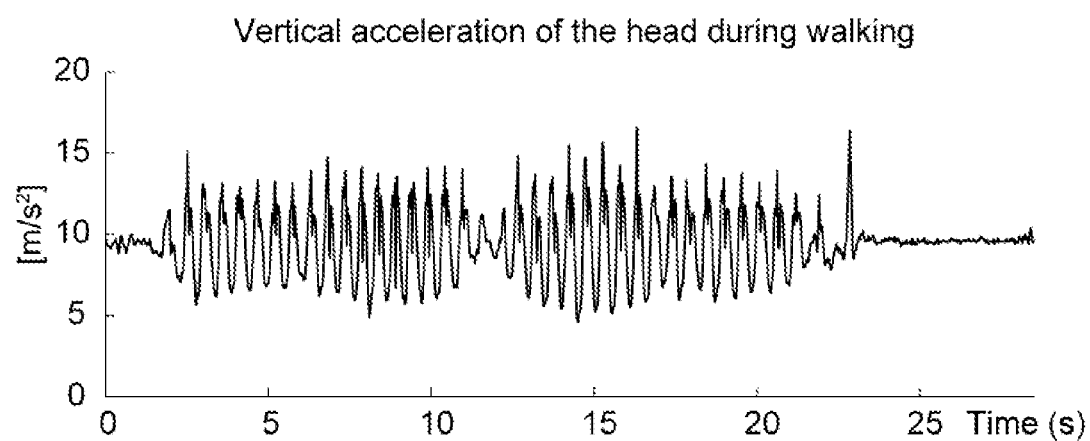
FIG. 3 is a graph showing vertical acceleration of a user's head as a function of time during locomotion.

In some embodiments, sensors 110, 112, and/or 134 include accelerometers and/or gyroscopes and/or magnetometers that measure movements of the head and body of the user of assistive device 100. For example, FIG. 3 is a graph that shows acceleration of a user's head (e.g., in the vertical direction approximately parallel to the user's spine) while the user is walking. The baseline acceleration is due to gravity. The rapid oscillations in the measured acceleration are due to up-and-down movements of the user's head with each step. The information shown in FIG. 3 can be transmitted to processor 130 for analysis. Processor 130, by analyzing the content of the measured acceleration signal in the time and/or frequency domains (e.g., by performing a Fourier transform analysis) can determine that the user of assistive device 100 is engaged in locomotion, and this information can be used to determine the activity of the user of device 100.

Figure 4A:
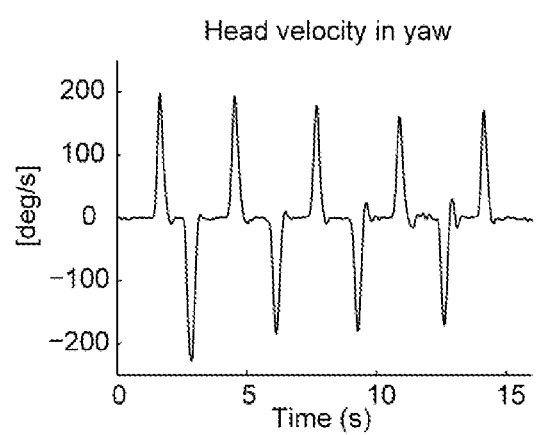
FIG. 4A is a graph showing head velocity as a function of time in the yaw plane for side-to-side head motion.
Figure 4B:
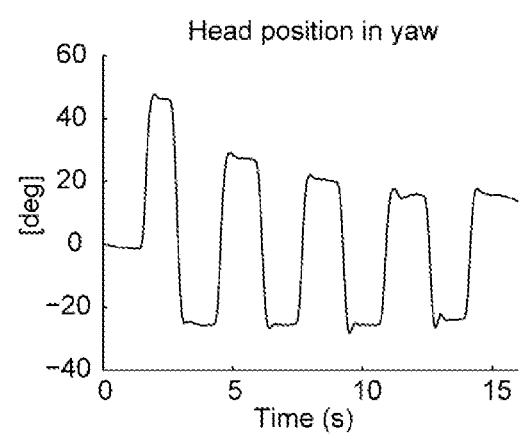
FIG. 4B is a graph showing head position as a function of time in the yaw plane for side-to-side head motion.

Motion of the head and/or body of the user can also occur during other types of activities, and can be measured using the same types of sensors (e.g., accelerometers and/or gyroscopes and/or magnetometers). For example, FIG. 4A is a graph showing angular velocity as a function of time in the yaw (e.g., side-to-side) plane for a user who is voluntarily swinging his or her head from side-to-side to follow a moving object, as might occur during a tennis match for example, while at the same time not undergoing any locomotion. FIG. 4B is a graph showing the measured position of the user's head as a function of time for the same voluntary motion. As is evident from FIG. 4A, the rapid changes in angular velocity of the user's head provide a temporal "signature" for voluntary head movement. Similarly, in FIG. 4B, the series of rapid changes in head position, followed by short periods in which the head position is relatively stable, also provide a temporal signature for voluntary head movement. Measured angular velocity and position information of the type shown in FIGS. 4A and 4B can be transmitted to processor 130 for analysis. On the basis of the distinctive features of shown in FIGS. 4A and 4B, processor 130 can identify when back-and-forth motion of the head of the user of assistive device 100 is voluntary on the part of the user.

Alternatively, in some embodiments, motion can be detected using an inertial measurement unit (IMU) that includes a 3-axis gyroscope and a 3-axis accelerometer. The IMU can be implemented as any of sensors 120, 122, and 134, for example, enclosed within or attached to frames 102 and/or housing 132. The sensor(s) can be configured to measure displacements and angular motion of the head and/or body of the user of assistive device 100 in three orthogonal coordinate directions and about each of three coordinate axes defined by the coordinate directions. To determine whether motion of the body of the user is occurring, linear acceleration (along one or more of the three coordinate directions) measured by the IMU is compared to a linear acceleration threshold value that defines a cutoff for motion detection. If the measured linear acceleration is below the threshold value, processor 130 concludes that no motion of the user's body is occurring (e.g., the user is not undergoing locomotion). In some embodiments, the linear acceleration threshold value can be $0.8 \pm 0.3$ m/s$^2$ above the acceleration due to gravity, for a duration of at least 20 ms. If this condition is satisfied, the user has transitioned from being still to moving. This threshold can be tuned for each user individually.

If the measured linear acceleration exceeds the threshold value, then vertical acceleration (e.g., in a direction approximately parallel to the user's spine) measured by the IMU is compared to a heel strike threshold value that defines a cutoff for walking by a person. This threshold value, like the linear acceleration threshold value discussed above, is adjustable to account for individual variations among users of the assistive device. If the measured vertical acceleration exceeds the heel strike threshold, processor 130 concludes that the user of assistive device 100 is walking. If the measured vertical acceleration does not exceed the heel strike threshold value, processor 130 concludes that motion of the user's body is occurring, but the motion is not due to walking. In certain embodiments, the heel strike threshold value for adults can be from 1.5 m/s$^2$ to 2.5 m/s$^2$.

As discussed previously, in some embodiments, sensors for measuring acceleration are present in both frames 102 and in housing 132. By using two sets of sensors, measurements of both linear and angular motion of the user's head (from the frames-mounted sensors) can be adjusted based on measurements of linear and angular motion of the user's body (from the housing-mounted sensors, which provide reference acceleration values).

Figure 7:
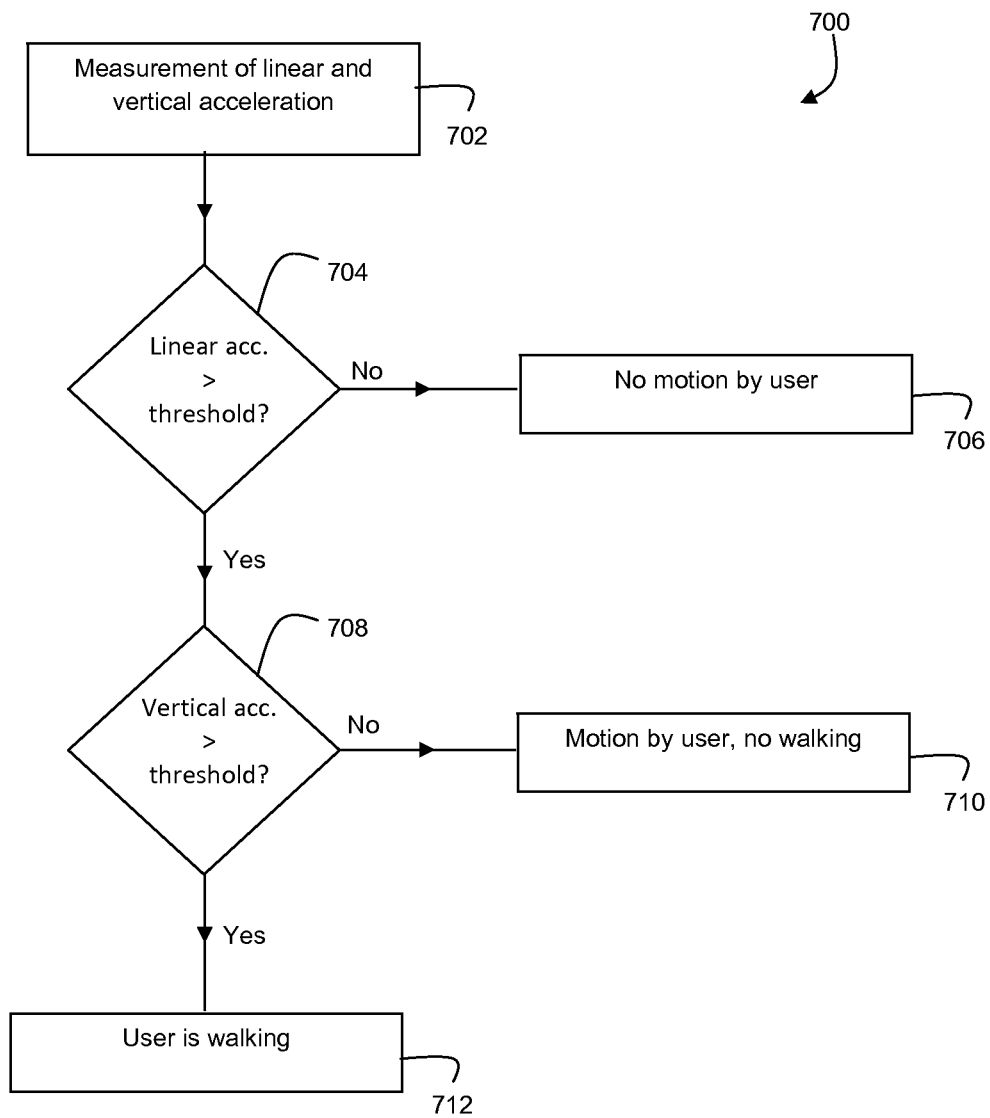
FIG. 7 is a flow chart showing steps for determining whether the user of an assistive device is walking.

Flow chart 700 in FIG. 7 shows a series of steps for determining whether a user of assistive device 100 is walking. In the flow chart, measurements of linear and vertical acceleration occur first in step 702, and then processor 130 determines in step 704 whether motion of the body of the user is occurring based on a comparison between the measured linear acceleration and the linear acceleration threshold value. If motion is not occurring, the analysis terminates in step 706. If motion is occurring, processor 130 then determines in step 708 whether the motion corresponds to locomotion by the user by comparing the measured vertical acceleration to the heel strike threshold value. If the measured vertical acceleration is greater than the heel strike threshold value, then processor 130 determines in step 712 that the user is walking. Otherwise, processor 130 determines in step 710 that the user is not walking (but is still in motion).

Additional systems and methods for detecting motion and determining the source of the motion that can be implemented in assistive device 100 are disclosed in U.S. Provisional Patent Application No. 61/555,908, the entire contents of which are incorporated herein by reference.

(b) Information about or from the Environment of the User

In addition to receiving information about the user's activity in the form of direct commands and/or indirect measurements, information about the environment of the user can be obtained by assistive device 100 through automatic monitoring of the environment using its various sensors. This information can include, but is not limited to, colors, sounds, voices and speech, faces, ambient illumination, the user's geographical position, the user's heading, the user's head and/or body gestures, objects in the user's environment, text in the user's environment, hazards, the direction of the user's gaze, and sources of sounds and/or lights. The following detailed discussion provides examples of the types of environment information that can be measured and transmitted to processor 130, but is not exhaustive, and other types of environment information can also be measured.

(i) Position and Location

In some embodiments, sensors in assistive device 100 can be configured to measure information that can be used by processor 130 to determine the position or location of the user. For example, sensors in assistive device 100 can be configured to receive GPS location signals and/or radiofrequency signals from RFID tags embedded in structures such as buildings, lamp posts, street signs, vehicles, and other structures. On the basis of these signals, processor 130 can determine the location of the user and/or the position of the user relative to a variety of objects and structures. Alternatively, or in addition, sensors in assistive device 100 can be configured to receive range finding signals from transmitters (e.g., ultrasonic and/or infrared signals), and processor 130 can determine the position of the user relative to other objects in the vicinity of the user based on the range finding signals.

In addition, other radiofrequency signals such as transponder signals and/or cellular radiofrequency signals can be detected and used by processor 130 to determine the location of the user. For example, processor 130 can estimate distances from signal transmitters based on the strength of detected radiofrequency signals. Alternatively, or in addition, processor 130 can determine the position of the user by triangulation based on measured signals from multiple transmitters.

(ii) Outdoors vs. Indoors

In some embodiments, processor 130 can also be configured to determine whether the user is indoors or outdoors. For example, measured GPS signals are typically of smaller intensity when a GPS receiver is indoors. By quantitatively comparing the magnitude of the detected GPS signal to a threshold signal magnitude, processor 130 can determine whether the user is indoors or outdoors. Alternatively, processor 130 can make the same determination if sensors in assistive device 100 detect radiofrequency signals from RFID tags that are known to be embedded inside buildings. Processor 130 can access a database of RFID tag locations (e.g., either stored in housing 132 or accessible wirelessly from a remote location) to determine whether particular detected signals correspond to interior or exterior tags.

Figure 6:
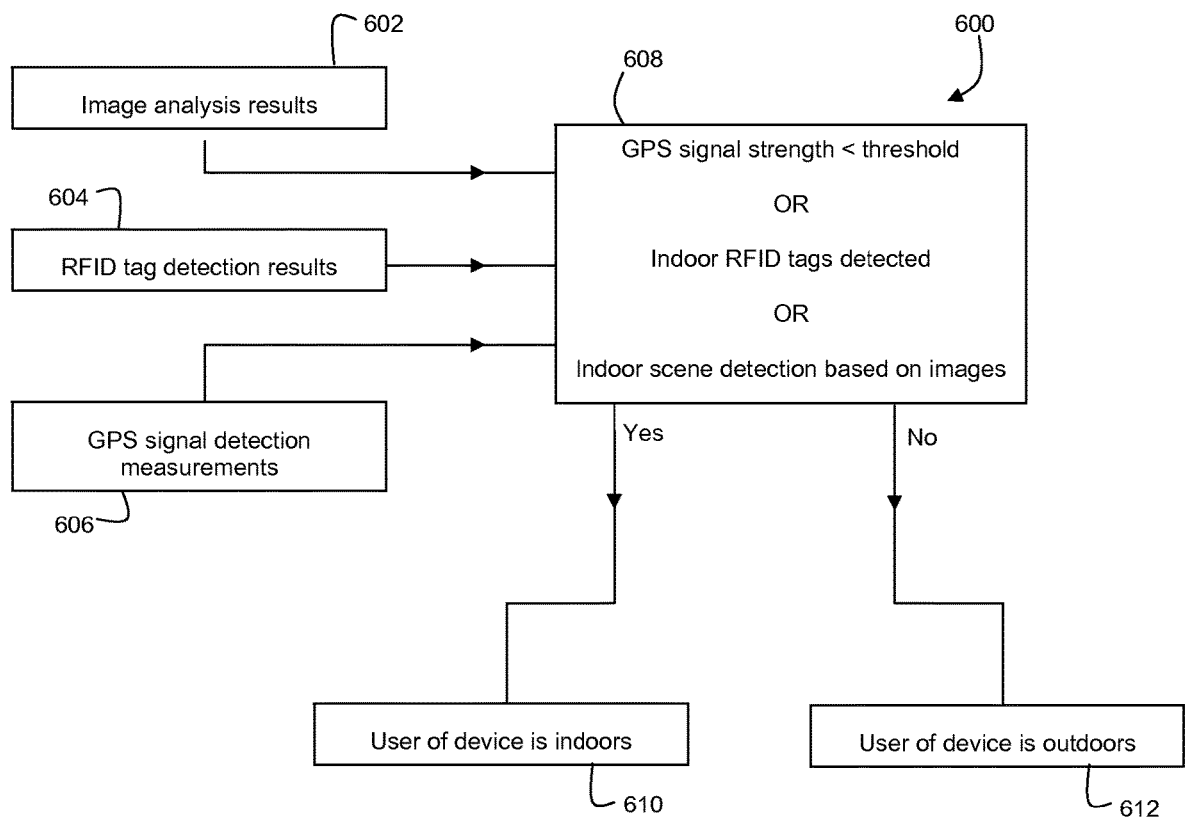
FIG. 6 is a flow chart showing steps for determining whether the user of an assistive device is indoors or outdoors.

FIG. 6 shows a flow chart 600 that illustrates relationships among different types of information measured by assistive device 100 and the determination of outdoor or indoor status by assistive device 100. As shown in FIG. 6, image analysis results can optionally be provided at step 602, RFID tag detection results can optionally be provided at step 604, and GPS signal detection measurements can optionally be provided at step 606. When some or all of these measurements are compared in step 608, if the measured GPS signal strength is less than a predefined threshold value, or if one or more "indoor" RFID tags are detected, or if analysis of images by processor 130 results in the recognition of indoor objects or features, processor 130 concludes that the user is indoors in step 610. If none of these conditions are satisfied, processor 130 concludes that the user is outdoors in step 612. Instructions issued either by the user or by a remote person with suitable permission can override the determination by processor 130.

In certain embodiments, processor 130 can be configured to determine whether the user is indoors or outdoors based on ambient light measurements. For example, sensor 120 and/or 122 can be radiation detectors (e.g., photodiodes, light meters, or similar devices) that measure ambient light intensity and/or spectrum in the vicinity of assistive device 100 and report the measured light intensity to processor 130. By comparing the ambient light intensity to a threshold value (which defines a cutoff between indoor and outdoor light intensity), processor 130 can determine whether the user is indoors or outdoors. Alternatively, or in addition, by comparing the ambient light spectrum to a reference spectrum (e.g., where the reference spectrum corresponds to either natural sunlight or indoor fluorescent lights), processor 130 can determine whether the user is indoors or outdoors.

In some embodiments, processor 130 can be configured to determine whether the user is indoors or outdoors based on temperature measurements. Sensor 120 and/or 122 can be temperature sensors that transmit information about the ambient temperature in the vicinity of assistive device 100 to processor 130. Processor 130 can then determine whether the user is outdoors depending upon the ambient temperature. For example, if the measured ambient temperature is greater than about 80° F. or less than about 60° F., processor 130 can conclude that the user is outdoors. Alternatively, if the measured temperature is between these upper and lower limits, it may not be possible—based on temperature measurements alone—to determine whether the user is indoors or outdoors. In such a case, other measurements disclosed herein can be used to make a determination.

(iii) Presence of People

In certain embodiments, processor 130 can be configured to determine if people are present within the vicinity of the user of assistive device 100. For example, sensors 120 and/or 122 measure audio signals which are transmitted to processor 130 for further analysis. Processor 130 can apply filtering algorithms to the detected audio signals to determine whether speech frequencies are present in the audio signals. If such signals are present, processor 130 concludes that people are present in the vicinity of the user of assistive device 100. Audio sensors can detect sounds in the user's environment that the user might not be able to detect naturally, and can transmit this auditory information to the user. Auditory information transmitted to the user can be amplified to make it understandable if the user is hearing impaired.

Figure 8:
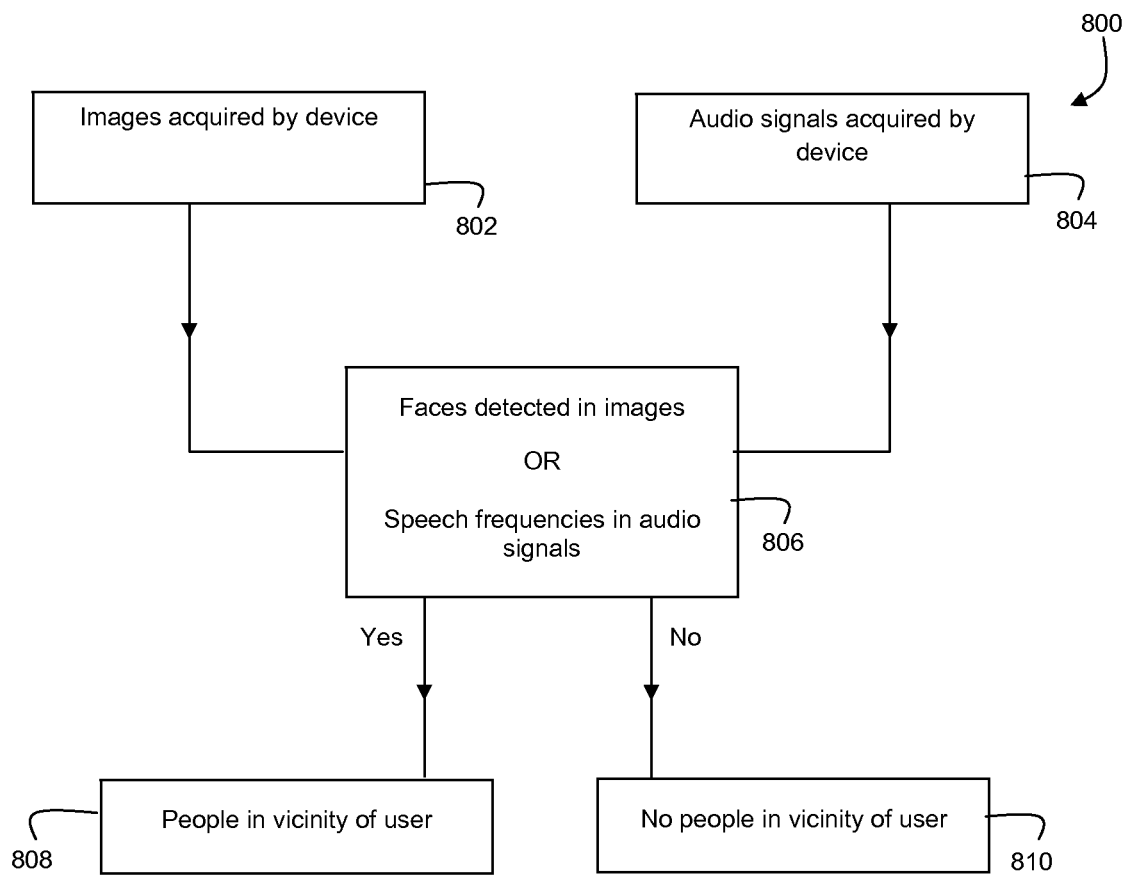
FIG. 8 is a flow chart showing steps for determining whether people are present in the vicinity of the user of an assistive device.

FIG. 8 shows a flow chart 800 that includes steps for determining whether one or more persons are present in the vicinity of the user of assistive device 100. In FIG. 8, visual information (e.g., one or more images) is optionally obtained by the device in step 802, and audio information (e.g., detected sounds) is optionally obtained by the device in step 804. The visual and/or audio information is transmitted to processor. By applying facial detection algorithms (to the visual information) and frequency and/or speech analysis algorithms (to the audio information) in step 806, processor 130 determined whether people are present 808, or not present 810, in the vicinity of the user of assistive device 100.

Returning to step 220 in FIG. 2, after assistive device 100 has obtained information from the user and from or about the environment of the user, processor 130 determines the activity of the user. In general, the activity of the user is determined by processor 130 based on a combination of the information obtained from the user and an analysis of the information about the environment of the user. In some embodiments, more specific rules for determining the activity of the user can be implemented. For example, when information about the activity of the user is obtained directly from the user (e.g., in the form of a verbal command), processor 130 can determine the activity of the user based solely on this information. Such activities can include, for example, navigating, eating, reading, requesting information from device 100, and a variety of other activities associated with everyday living.

As another example, when direct information is not obtained from the user (e.g., if the user of device 100 remains silent and does not issue any verbal or other commands), processor 130 can determine the activity of the user based on indirect information from the user (if available) and information about the user's environment.

In analyzing information about the user's environment, processor 130 can apply algorithms to determine, for example, whether the user is indoors or outdoors based on objects recognized in images. Processor 130 can also apply algorithms to determine whether faces of people appear in images, whether signs with text appear in images, and whether other sources of text are present in images. Facial detection and/or recognition algorithms that can be used to detect faces in images can include, for example, Haar filters, which can be used in conjunction with a database of faces stored in housing 132, or on a server that can be accessed by processor 130 (e.g., via a wireless link to the internet, or to a cloud computing system). As will be discussed later, processor 130 can also identify individual persons by comparing detected faces to databases of personal information stored either within housing 132 or on remote computing devices that are accessed by processor 130 (e.g., on distributed cloud computing networks). Further, as discussed previously, audio signals detected by the sensors in assistive device 100 can also be used by processor 130 to determine whether people are present in the vicinity of assistive device 100 through speech detection algorithms and analysis methods (e.g., Fourier transform analysis methods).

Using the foregoing information collected by the device's sensors, processor 130 can determine an activity of the user even when the user does not issue direct commands to the device. For example, as explained above, processor 130 can determine that the user is navigating (e.g., undergoing locomotion) by measuring motion of the user's head and body using accelerometers and gyroscope sensors. As another example, processor 130 can determine that the user is reading by detecting text in visual information collected by the device's detectors. The determination by processor 130 can be made based not only on the presence of text in visual information, but also on the properties of the text. Thus, for example, processor 130 can analyze the visual information when text is detected to determine a distance between the text and the user. If the distance is less than a distance threshold, e.g., 14, 16, 18, 20, 22, 24, 26, 28, or 30 inches, then processor 130 determines that the user is likely interested in trying to read the text (in which case the text might be audibly read to the user). If the distance is more than the distance threshold, then processor 130 determines that the user is not engaged in the activity of reading (e.g., such a situation might arise if the user was navigating a street, and visual information from street signs was collected, but might not be audibly read to the user and is instead "read" internally and used for other functions). As will be discussed later, whether or not the text is converted to audio signals and transmitted to the user depends on different sets of rules for different activities. As a further example, processor 130 can determine that the user is eating by detecting objects such as glassware, utensils, tableware, and certain types of text (e.g., menus) among visual information obtained using the device's detectors.

In general, device 100 is configured to recognize a wide variety of different user activities. These can include, for example, tasks associated with everyday living such as: navigation (indoors or outdoors); presence in specific types of buildings and/or at specific locations such as the user's home, parks, grocery stores, drug stores, banks, transit hubs such as train stations, bus stations, subway stations, and airports; reading; conversing with others; eating; and counting money. In the following discussion, examples of different activities recognized by device 100 are provided in more detail. However, the discussion of recognized activities is not exhaustive, and other activities can also be recognized by device 100. In addition, the user and/or other approved third parties can define additional activities that device 100 can recognize, and the definitions associated with the additional activities can be stored in a memory unit of device 100.

As discussed above, in some embodiments, device 100 recognizes that the user is engaged in the activity of outdoor navigation. When this activity is recognized, processor 130 uses the sensors and detectors of device 100 to collect information about the user's environment such as potentially hazardous objects (e.g., cars, garbage receptacles, curbs, holes, steps) that lie in front of the user, and various landmarks (e.g., streets, cross-walks, and intersections). Processor 130 can apply distance estimation algorithms to visual information about the user's environment and/or use information derived from measurement of range finding signals by one or more sensors to estimate the distance between various objects and the user.

Processor 130 (in subsequent steps of the process shown in FIG. 2) can provide audio and/or tactile feedback to the user regarding the presence and proximity of such objects. For example, processor 130 can transmit location information via audio and/or tactile signals to the user (e.g., vibrotactile signals increase in magnitude and/or frequency as the user approaches a location pre-selected by the user). Vibrotactile signals can be used to "steer" the user around objects or along the center of a walkway. Processor 130 can also transmit an audio indicator signal when a pre-determined target destination has been reached, and audio signals when the user's path deviates from the most direct or a pre-selected route from the user to the destination. In certain embodiments, both vibrotactile and audio information can be transmitted to the user to assist in navigation and hazard avoidance. In some implementations, vibrotactile information more efficiently communicates fine directional adjustments to a user, and audio information more efficiently directs the user to perform coarser directional adjustments.

As discussed above, in certain embodiments, device 100 recognizes that the user is engaged in the activity of indoor navigation. When this activity is recognized, processor 130 uses the sensors and detectors of device 100 to collect information about the user's environment such as potentially hazardous objects, and can implement (in subsequent steps of the process shown in FIG. 2) both distance and angular filters such that only information about objects within a certain threshold distance and within a certain range of angles relative to the user is reported to the user. The threshold distance can be, for example, 50 feet or less (e.g., 40 feet or less, 30 feet or less, 20 feet or less, 10 feet or less). The angular range can be, for example, a forward-looking 90 degree range (e.g., 70 degree range, 60 degree range, 50 degree range, 40 degree range). The implementation of distance and angular filters reduces the amount of information that processor 130 analyzes, reducing the overall power consumption of device 100.

In subsequent steps of FIG. 2, processor 130 can also use facial recognition algorithms to identify for the user people whose faces appear in collected visual information, and can use way-finding algorithms for navigating within specific buildings, depending upon the location of the user. For example, maps of individual buildings are accessible to processor 130 through databases as described herein, and can be used to guide the user through such buildings in pursuit of a specific target (e.g., a location or room within the building). Processor 130 can apply object recognition algorithms to visual information to identify and report to the user certain features within the building such as specific rooms (e.g., lobby), elevators, and signs. Processor 130 can use this information to provide navigational information to the user of device 100.

In some embodiments, device 100 recognizes that the user is engaged in the activity of finding a specific person. Accordingly, processor 130 can use the detectors of device 100 to collection visual information about the user's environment, and then (in subsequent steps of the process shown in FIG. 2) apply facial recognition algorithms to the visual information to identify the specific person of interest. Processor 130 can provide to the user audio and/or tactile signals that identify different people in the environment of the user, that indicate distances between identified persons and the user, and that announce when the person of interest is present. Processor 130 can also identify the location of a person of interest by detecting the person's voice in audio information measured using the sensors of device 100. Alternatively, or in addition, location information can also be provided by devices worn by people of interest (e.g., portable identification devices) to facilitate their localization.

In certain embodiments, device 100 recognizes that the user is engaged in the activity of undergoing a monetary transaction. Processor 130 can apply algorithms to visual information collected by the detectors of device 100 to report differences among different monetary denominations to the user (e.g., to advise the user of the amount of money in his or her hands).

In some embodiments, device 100 recognizes that the user is engaged in the activity of conversation with another person. Processor 130 can apply algorithms to visual information collected by the detectors of device 100 to report to the user facial expressions of persons in the vicinity of the user, to provide him or her with important emotional contextual information.

In certain embodiments, device 100 recognizes that the user is engaged in the activity of reading (e.g., based on a verbal command from the user, activation of a switch or other hardware control, based on detection of text in visual information collected using the detectors of device 100, and/or based on detection of the user's hand or fingers pointing to text in the visual information. Processor 130 can apply algorithms to analyze the context in which the text appears. For example, when text appears on a sign or banner, processor 130 can construct an electronic spoken representation of the text which is transmitted to the user. When processor 130 identifies text on a page of a book, magazine, or other printed material, and when a finger of the user is identified as being positioned over a portion of the text, processor 130 can construct an electronic spoken representation of the words of the text in proximity to the user's finger. Processor 130 can monitor the position of the user's finger so that by translating his or her finger along lines of text, the user can induce processor 130 to "read" the text aloud. Alternatively, or in addition, the sequence of text that is read to the user can be selected by monitoring the position of the user's eyes (e.g., using RF coils and/or cameras, as disclosed herein). In certain embodiments, processor 130 can be configured to read languages other than English and/or to translate text in one language to spoken words in another language selected by the user.

After the activity of the user has been determined in step 220, processor 130 then filters the information about the user's environment obtained by the sensors of device 100 based on the user's activity, as shown in step 230. In general, the step of filtering the environment information based on the user's activity reduces the amount of information that is transmitted to a user so that only the information that is relevant to the user is transmitted. By filtering the information, the user is not overwhelmed by the amount of information that is transmitted, and the computational load on the system is reduced. At the same time, by ensuring that the information relevant to the user's current activity is transmitted, the system enables the user to interact with his or her environment in a meaningful way.

Figure 10:
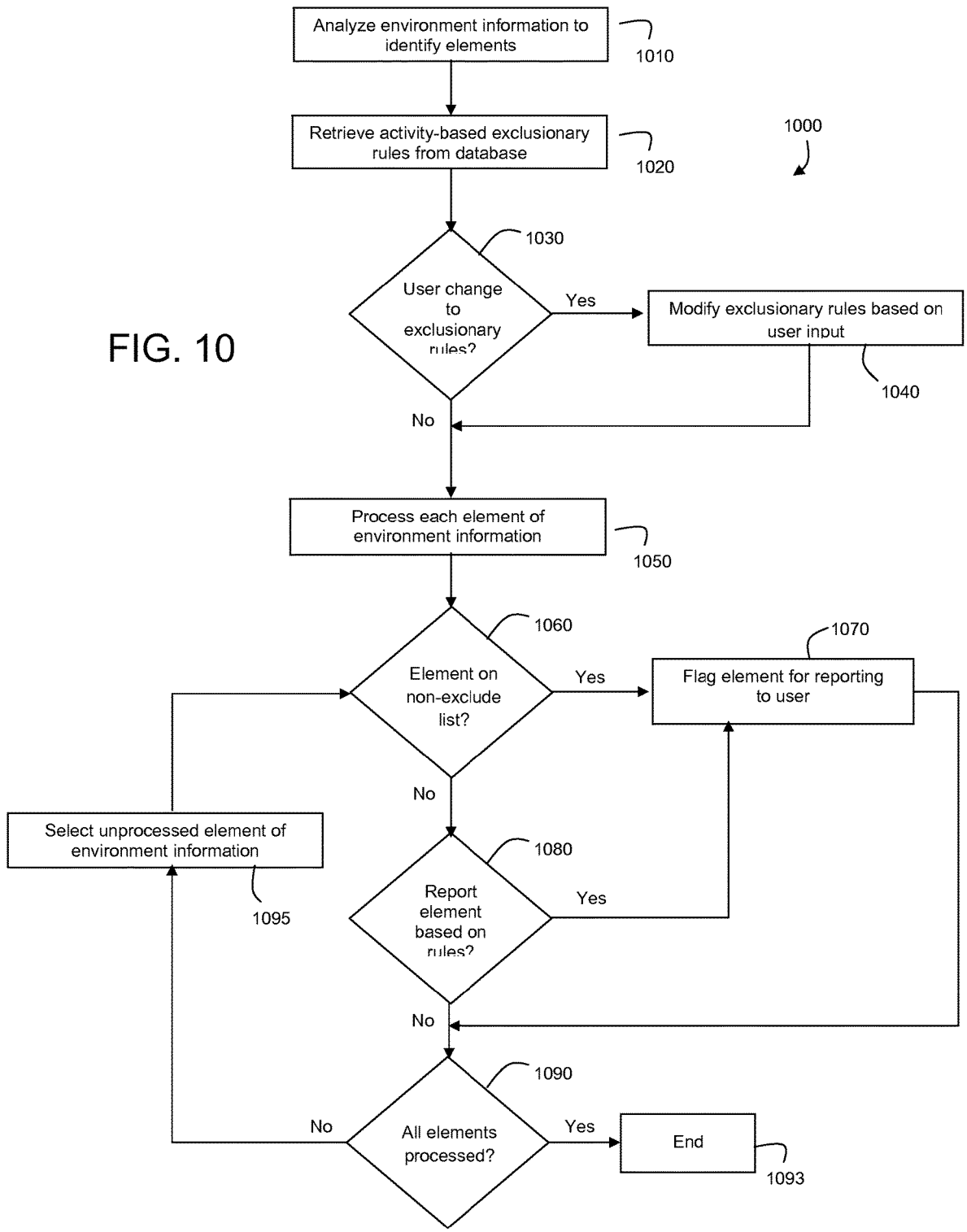
FIG. 10 is a flow chart showing steps for filtering information about a user's environment.

Filtering the environment information based on the user's activity typically involves a number of steps. FIG. 10 is a flow chart 1000 that shows a series of steps for filtering environment information based on a user's activity. In step 1010, the environment information is analyzed to identify specific elements of the information. The elements of the information can include, for example, objects such as buildings, signs, landmarks, guideposts, cars, money, and, more generally, a wide variety of structures and articles. Elements of the information can also include portions of text, people, faces, and animals. Further, elements of the information can include sounds (including speech, non-speech, and non-verbal sounds), distances, orientations, positions, and other spatial relationships. More generally, the elements of the information correspond to all of the various features that can be extracted from the environment information that describe the objects, people, and attributes of the user's environment.

To identify the elements of the environment information, the systems and methods disclosed herein apply a variety of algorithms to process the information received by the device's detectors and sensors. For example, processor 130 can use many different types of image processing algorithms to analyze visual information about the user's environment, including
object recognition algorithms, facial recognition algorithms, optical character recognition and text recognition algorithms, and distance-estimating algorithms. Object recognition algorithms in conjunction with bimodal color histograms and/or edge detection algorithms can be used to identify signs and other indicators in visual information. Further, algorithms for estimating the ambient light intensity in the visual information can be used by processor 130 to determine whether device 100 is indoors or outdoors. Such measurements can be used as an alternative to, or in addition to, other measurements of ambient light intensity discussed herein.

In certain embodiments, the identification of elements at this stage (i.e., in step 1010) does not involve the refinement of those elements. For example, processor 130 can apply a variety of algorithms to locate objects in visual information, without identifying what the objects are. Similarly, processor 130 can apply algorithms to locate faces in visual information without identifying the persons to whom the faces belong. Such identification steps can involve more intensive processing and/or access to databases of information, which can be more computationally- and power-intensive than simply identifying the elements. As a result, the refinement of the elements can be deferred to later processing steps, when some of the elements may have been filtered out, thereby reducing the device's overall computing load.

Examples of useful object recognition and classification algorithms are disclosed in the following, the entire contents of each of which is incorporated by reference herein: U.S. Pat. Nos. 5,850,470 and 8,015,132; J. Xiao et al., "SUN Database: Large Scale Scene Recognition from Abbey to Zoo," IEEE Conference on Computer Vision and Pattern Recognition (2010), pp. 3485-3492; and Quattoni et al., "Recognizing Indoor Scenes," IEEE Conference on Computer Vision and Pattern Recognition (2009), pp. 413-420.

Examples of facial recognition algorithms are disclosed in the following references, the entire contents of each of which are incorporated herein by reference: U.S. Pat. Nos. 5,642,431 and 5,835,616; Viola et al., "Rapid Object Detection using a Boosted Cascade of Simple Features," IEEE Conference on Computer Vision and Pattern Recognition (2001), pp. 511-518; and Turk et al., "Eigenfaces for Recognition," J. Cognitive Neuroscience 3(1): 71-86 (1991).

Examples of text recognition algorithms are disclosed in U.S. Pat. Nos. 6,446,041; 7,805,307; 8,009,928; and 8,014,604, and at internet address code.google.com/p/tesseract-ocr/, the entire contents of each of which are incorporated herein by reference.

Examples of speech recognition algorithms are disclosed in U.S. Pat. No. 6,161,091, the entire contents of which are incorporated herein by reference.

A variety of different methods for measuring range finding signals and performing distance estimation can be used, including methods based on the use of multiple cameras (which can be used to provide stereo input), on acoustic wave detection, on methods that determine distance by measuring changes in the dimensions of objects in the environment of the user as the user approaches the objects, and on laser range-finding. In addition to measuring distances and angular orientations of objects with respect to the user, processor 130 can use distance information measured with these methods as a function of time to estimate "time to impact" of objects that are approaching the user. Alternatively, or in addition, processor 130 can use multiple methods of measuring distances (e.g., methods based on measuring changes in the dimensions of objects, and methods based on detected reflected acoustic waves from objects) to estimate time to impact for objects. The estimations can also be based on changes in position information about the user (e.g., the rate and direction in which the user is moving through his or her environment). Examples of systems and methods are disclosed, for example, in the following U.S. Patents, the entire contents of each of which are incorporated herein by reference: U.S. Pat. Nos. 4,992,998; 6,104,671; 6,411,327; and 8,018,580.

In some embodiments, processor 130 can also access databases of stored information to identify elements of the environment information. Such databases can be stored locally on device 100 and/or can be stored remotely and accessed by processor 130 over a distributed network. In general, wired and/or wireless communication between device 100 and distributed networks such as a computing "cloud" can be implemented in various ways. In some embodiments, device 100 can be configured to retrieve a variety of information stored in storage and/or computing devices also connected to the distributed networks. For example, databases available to device 100 for identification of elements of the environment information can include: information about the layout of streets, buildings, geographical landmarks, and other cartographic features; information about the interior layout of buildings; information about local points of interest; navigation information, including road closures, road work, and information comparing alternative routes between two locations; libraries of faces for input to facial recognition algorithms; libraries of objects for object recognition algorithms; and samples of text in various styles for optical character recognition algorithms.

In addition to generalized databases of information, device 100 can also access one or more "personalized" databases that store information specific to the user of the assistive device. Such databases can be stored in a storage unit integrated into device 100, and/or in one or more devices in the distributed network. Personalized databases can include information such as cartographic and navigational information about places that the user frequently visits and faces of people that the user frequently encounters, for example.

Device 100 can access a wide variety of distributed networks. Such networks can, in turn, include a variety of computing devices in communication with one another, including computers, mobile phones, GPS transceivers, and other computing devices. Device 100 can be configured to access such networks directly (e.g., using a transceiver connected to processor 130). Alternatively, or in addition, device 100 can be configured to connect to another computing device such as a mobile phone, and to communicate with devices in the distributed network through the mobile phone. Such a configuration can ensure that the power requirements of device 100 remain modest.

In certain embodiments, assistive device 100 can be configured to offload certain processing tasks to computing devices located on the distributed computing network. In general, any of the steps disclosed herein can be performed by a computing device on the network and the results communicated to device 100 (e.g., to processor 130). For example, in step 1010, some or all of the steps involved in analyzing the environment information to identify elements of the information can be offloaded to a remote computing device (or, more generally, a remote electronic processor) on a distributed network. The remote computing device can analyze the environment information and report the identified elements to processor 130 over the network.

Various aspects and features of distributed computing environments are disclosed, for example, in U.S. Patent Application Publication No. US 2010/0241741, the entire contents of which are incorporated by reference herein.

After the elements of the environment information have been disclosed in step 1010, an activity-based set of exclusionary rules is retrieved from a database in step 1020. As discussed above, the database can be stored locally on device 100 or on a remote computing device accessible over a distributed network. The set of exclusionary rules defines, for the particular activity in which the user is engaged, which elements of the environment information will be transmitted to the user and which elements will not. Generally, elements not defined in the exclusionary rules are not transmitted to the user.

Typically, different activities have different sets of exclusionary rules. For example, the set of exclusionary rules for the activity of navigating includes reporting to the user objects within a certain threshold distance, objects within a certain field of view angular range, objects approaching the user at a rate of speed that exceeds a certain threshold rate, objects that correspond to signs, and objects or circumstances that correspond to hazards (e.g., information about road work ahead of the user). As another example, the set of exclusionary rules for the activity of eating includes reporting to the user objects such as glasses, tableware and glassware, faces within a certain threshold distance to the user, and portions of text within a certain threshold distance to the user.

Next, in step 1030, processor 130 determines whether the exclusionary rules retrieved in step 1020 should be changed based on user input. Input from the user can be obtained in a variety of ways. In some embodiments, the user can issue verbal commands to device 100 to modify the exclusionary rules. For example, the user can instruct device 100 to report all elements corresponding to automobiles in the environment of the user, even if some of these elements are farther away from the user than a threshold distance (and so would ordinarily be filtered out). In certain embodiments, the user can modify the exclusionary rules by issuing commands through activating controls on device 100 such as a touch-screen, sliders, or buttons. In some embodiments, a third party such as a person remotely monitoring device 100 can issue commands to modify the exclusionary rules (e.g., through a user interface to a computing device) which are transmitted to device 100. If instructions in any form are received from the user or an approved third party to modify the exclusionary rules, then the rules are modified in step 1040. At the user's option, the modified exclusionary rules can be saved permanently in the database.

Then, in step 1050, each identified element of the environment information from step 1010 is processed according to the exclusionary rules to implement the filtering of the environment information. In the first processing step 1060, processor 130 determines whether the element being processed is on a non-exclude list. Device 100 can include, either stored internally or on a network-accessible remote computing device, a list of elements that should never be excluded from transmission to the user. In other words, each element on the non-exclude list is always transmitted to the user. The list of element on the non-exclude list can vary and can be modified by the user. In some embodiments, for example, the non-exclude list features hazards, text, and faces. Thus, device 100 will always transmit to the user information about hazards, text, and faces in the environment of the user. More generally, any of the elements that device 100 is capable of identifying can be featured on the non-exclude list.

If the particular element that is being processed appears on the non-exclude list, then the element is flagged for reporting to the user in step 1070. If not, then the exclusionary rules (including any modifications from step 1040) are applied to determine whether the element being processed should be reported to the user in step 1080. If the element should be reported, it is flagged for reporting in step 1070.

Next, in step 1090, if all identified elements of the environment information have been processed, then filtering ends at step 1093. If not all elements have been processed, then an unprocessed element of the environment information is selected at step 1095, and control returns to step 1060.

Returning to FIG. 2, after the information about the user's environment has been filtered in step 230, the configuration of device 100 can optionally be adjusted in step 240 according to the exclusionary rules obtained in step 230. The process for adjusting the configuration of device 100 will be discussed later in connection with FIG. 13.

In the next step 250, the filtered information is prioritized before reporting to the user. In general, prioritizing the filtered information helps to ensure that the information reported to the user, in addition to being relevant to the user's activity, is also conveyed according to its relative importance to the user's activity. That is, while the filtered information can include multiple elements relevant to the user's activity, certain elements may be more relevant or important than others, and should therefore be reported first. For example, for a user navigating a busy street, elements that correspond to hazards and signs may be more important than elements corresponding to faces of other pedestrians, even though each of these types of elements is relevant enough to report to the user. In step 250, the elements of the filtered information are prioritized for reporting to the user to account for the differences in relevance among the different elements to the user's activity.

Figure 11:
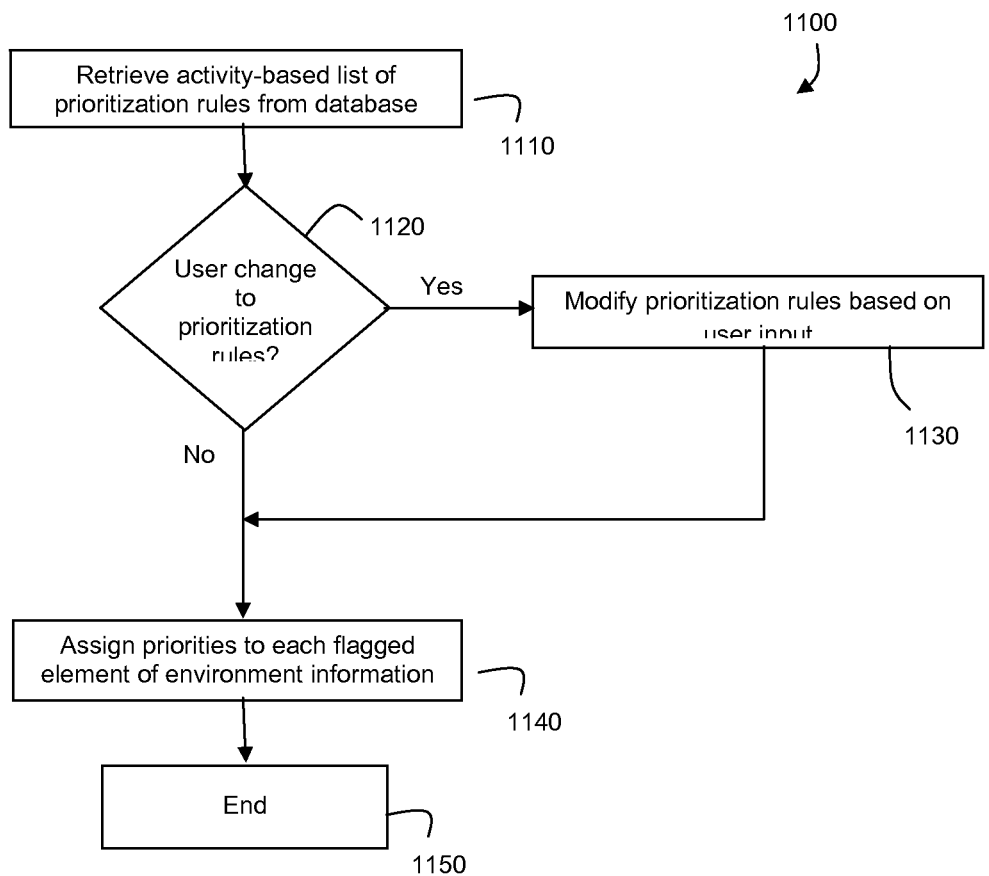
FIG. 11 is a flow chart showing steps for assigning reporting priorities to elements of information about a user's environment.

In general, prioritizing the elements of the filtered information involves a number of steps. FIG. 11 is a flow chart 1100 that includes a series of steps for prioritizing these elements. In a first step 1110, a list of prioritization rules is retrieved from a database according to the user's activity determined in step 220 of FIG. 2. The list of prioritization rules sets forth, for each activity of the user, the order in which elements of the filtered information are reported to the user. As an example, for the activity of outdoor navigation, the prioritization rules can specify that elements corresponding to hazards be reported first, followed in order by elements corresponding to other obstacles second, landmarks third, distance to a navigational target fourth, GPS positioning information fifth, text on signs sixth, and faces of others seventh. As another example, for the activity of reading, the prioritization rules can specify that elements corresponding to headlines be reported first, followed in order by elements corresponding to subtitles, large text passages, and legends under figures. As a further example, for the activity of eating, the prioritization rules can specify that elements corresponding to tables be reported first, followed in order by elements corresponding to chairs, glasses, utensils, and faces of people within a certain threshold distance from the user.

In general, the same type of information can be prioritized differently based on the activity of the user. For example, in many situations, there is likely to be a significant amount of text in the environment of the user. Transmission of the detected text, however, is prioritized based on the activity of the user. For example, if the user is engaged in the activity of reading, then text in the foreground (e.g., at a distance from the user that is less than a relatively short threshold distance such as 16 or 18 inches) is highly prioritized for transmission, as this text is likely to correspond to what the user is reading. Text in the background (e.g., at a distance greater than the threshold distance from the user) is assigned a relatively low priority, or is not transmitted to the user at all. In contrast, if the user is engaged in the activity of navigation, then text at a distance greater than the threshold distance is assigned a high priority, as this text is relevant to navigation. For example, the user can direct device 100 (e.g., through a verbal command) to navigate to a particular address, and processor 130 can capture and analyze text from visual information received by device 100 to locate the address on a building and direct the user to the building.

The ordering of elements specified by the prioritization rules retrieved from the database can, in general, take any form. Moreover, the user can change the prioritization rules for any one or more activities recognized by device 100. The next step 1120 in flow chart 1100 involves determining whether the user has initiated a change to the prioritization rules. As explained above in connection with FIG. 10, the user can modify the prioritization rules in different ways. In some embodiments, the user can issue verbal commands to modify the prioritization rules, e.g., instructing device 100 to elevate in priority the reporting of text on signs in the user's environment during navigation. In certain embodiments, the user can use controls such as buttons, sliders, or a touch-screen interface to modify the prioritization rules. If the user initiates a change to the prioritization rules, then the rules are modified in step 1130. Such changes can be made permanent in the database at the user's option.

Next, in step 1140, the prioritization rules (which may have been modified by the user) are applied to assign reporting priorities to each of the elements of the filtered information. The reporting priorities establish the order in which these elements are reported to the user. In general, the elements are reported in sequential, hierarchical fashion, beginning with the highest priority element. After the priorities have been assigned, the process terminates at step 1150.

Returning to FIG. 2, after the filtered information has been prioritized in step 250, the configuration of device 100 can optionally be adjusted in step 260 based on the prioritization of elements established in step 250. The process for adjusting the configuration of device 100 will be discussed later in connection with FIG. 13.

Next, in step 270, the elements of the filtered information which have been prioritized for reporting to the user in step 250 are refined. Refinement generally refers to a step in which elements that are located in the user's environment information (e.g., as part of filtering step 230) are further analyzed to determine additional information about the elements. For certain elements, this additional information may already have been determined as part of either step 230 or step 250, so no further refinement may be possible or desirable. For other elements, however, refinement provides more specific information about features of the user's environment.

A wide variety of refinements of the elements of the environment information can be implemented by processor 130. For example, objects that were located in visual information in step 230 can be refined to identify the objects in step 270 by applying object recognition and/or identification algorithms. Faces that were located in the visual information can be refined to identify the faces by applying face recognition and/or identification algorithms. Expressions on the faces can also be identified by applying suitable algorithms. Voices that were detected in audio information measured by the sensors of detector 100 can be refined to identify the speakers by applying voice recognition and/or identification algorithms. Text that was located in visual information can be refined by applying optical character recognition algorithms. Algorithms used by processor 130 to refine the elements of the filtered information can be the same as the algorithms used to locate the elements in step 230, as discussed above.

In step 280, the refined elements of the filtered information are re-prioritized for reporting to the user. Re-prioritization of the refined elements is an adaptive step that adjusts the reporting of information so that the information is delivered to the user in a timely manner, according to the circumstances of the user's activity. In particular, as the user interacts with his or her environment, the relationship between the user and his or her environment can change due to the actions of the user and changes in the environment. As a result, the initial prioritization established in step 260 may no longer be optimal after the user has been performing a particular activity for some time. The re-prioritization accounts for these changing circumstances, and also for commands issued by the user to re-configure operation of device 100.

Figure 12:
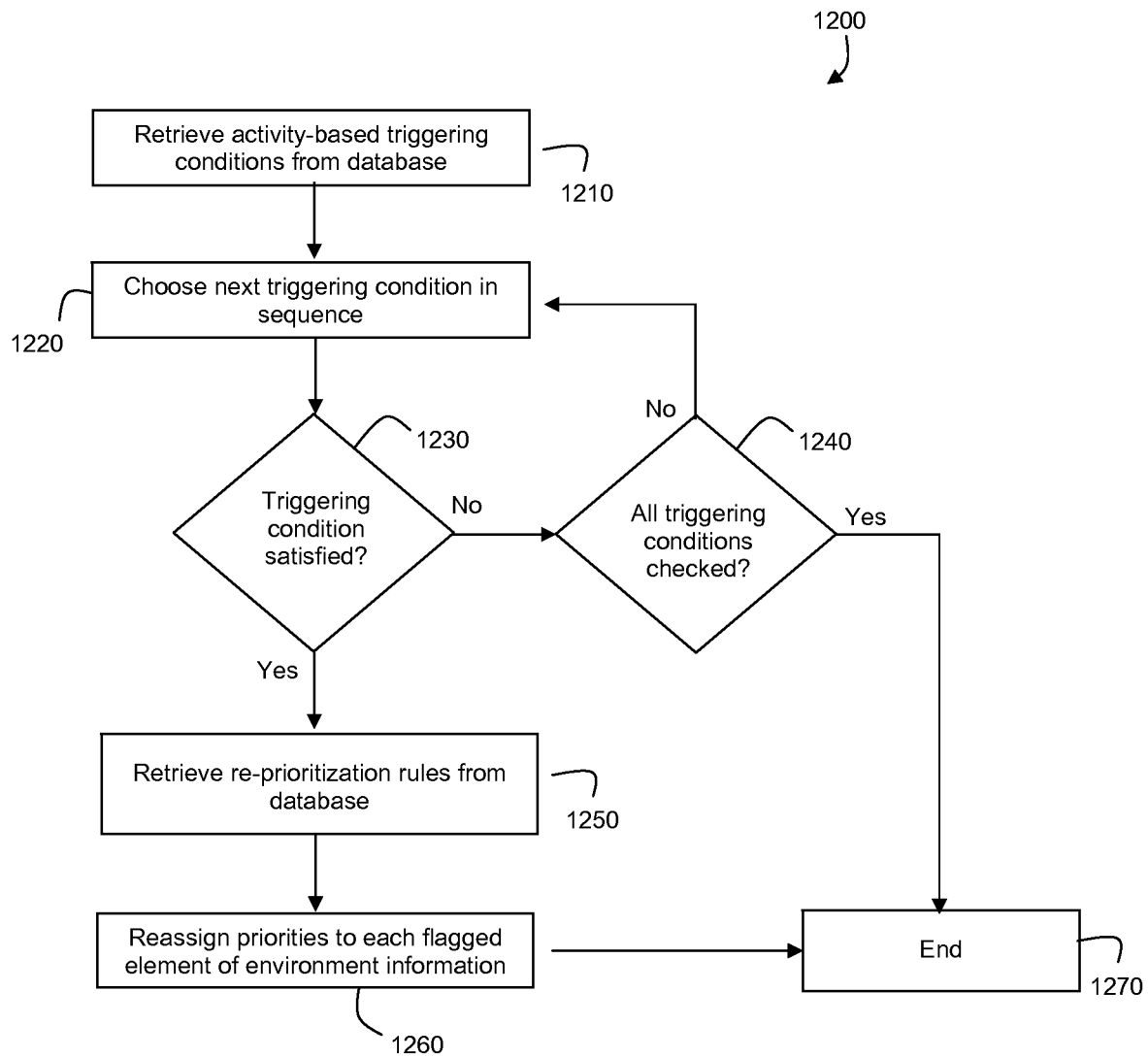
FIG. 12 is a flow chart showing steps for re-prioritizing elements of information about a user's environment for reporting to the user.

The process of re-prioritizing the refined elements for reporting generally includes a number of steps. FIG. 12 shows a flow chart 1200 that includes a number of steps for re-prioritizing refined elements. In a first step 1210, processor 130 retrieves a set of activity-based triggering conditions from a database. The set of triggering conditions defines, for the particular activity of the user determined in step 220 of FIG. 2, the circumstances in which re-prioritization of the refined elements occurs.

In general, any number of triggering events can be defined for each user activity, and the user can edit, delete, and/or add new triggering events as desired. The triggering events are specific to the activity for which they are defined, although the same triggering events can be defined for different activities. Further, a wide variety of different triggering events can be defined. As an example, for the activity of outdoor navigation, a hazard reporting triggering event can be defined such that re-prioritization occurs if a distance between the user and a hazard is less than a threshold distance. As another example, a triggering event can be defined such that a re-prioritization occurs if a relative rate of speed between the user and an object in the environment is more than a threshold speed. As a further example, a triggering event can be defined such that a re-prioritization occurs if the distance between the user and a navigation target or a location where the user should change direction is less than a threshold distance. As another example, a triggering event can be defined such that a re-prioritization occurs if the user crosses a barrier into a hazardous or forbidden area (such as entering into a room that is marked "restricted entry" or "hazardous"). For the activity of conversation with another person, a triggering event can be defined such that a re-prioritization occurs if the person's facial expression changes.

Although the above triggering events are likely to occur nearly instantaneously, triggering events can also be defined for circumstances that are likely to exist for longer periods of time. For example, a triggering event can be defined such that a re-prioritization occurs if the user is navigating and is not close to an important landmark. As another example, a triggering event can be defined such that a re-prioritization occurs if a large number of similar obstacles (e.g., trees) are present at less than a threshold distance in the user's environment. As a further example, a triggering event can be defined such that a re-prioritization occurs if when a person approaches the user at a distance of less than a threshold distance, and that person has previously been identified to the user.

After the triggering events have been retrieved in step 1210, each of the triggering events corresponding to the user's activity is checked in priority sequence, with the highest priority event checked first, to determine whether a triggering event has occurred. The highest priority event is selected in step 1220, and checked in step 1230 to determine whether it has occurred. If it has occurred, control passes to step 1250. If not, control passes to step 1240, where processor 130 determines whether all triggering conditions have been checked. If all conditions have been checked (and none have been triggered), the process ends at step 1270. However, if not all conditions have been checked, control returns to step 1220 where a new triggering condition is chosen and checked for occurrence.

If step 1250 is reached, then a triggering event has occurred, and the event that occurred is the highest priority event that occurred. Following detection of the triggering event, processor 130 then retrieves re-prioritization rules specific to the triggering event that occurred from a database in step 1250. The re-prioritization rules can, in general, take a wide variety of forms such as lists of hierarchical rankings of elements for reporting to the user, and conditional statements that prioritize certain elements with respect to others. As an example, if the triggered event corresponds to a distance between the user and a hazard being less than a threshold distance, or to a relative rate of speed between the user and an object that exceeds a threshold speed, then the re-prioritization rules can elevate the reporting of the hazard or object a higher (e.g., highest) priority. As another example, if the triggered event corresponds to a distance between the user and a navigation target, or location where the user should change direction, of less than a threshold distance, then the re-prioritization rules can elevate the reporting of the approaching landmark or navigation target to a higher (or highest) priority.

As a further example, if a triggering event corresponds to the user crossing a barrier into a hazardous or forbidden area, then the re-prioritization rules can elevate reporting of the direction of, and distance to, the barrier to a higher (or highest) priority. As an additional example, if a triggering event corresponds to a change in a facial expression of a person with whom the user is conversing, then the re-prioritization rules can elevate reporting of the person's facial expression to a higher (or highest) priority.

Re-prioritization rules can also cause certain elements of information to be reduced in priority. For example, if a triggering event corresponds to a user navigating far from any important landmarks, then re-prioritization rules can reduce the priority of reporting guidance information to the user, as in general, guidance information is only useful when it is reported relative to such landmarks. As another example, if a triggering event corresponds to a large number of similar obstacles present within a threshold distance of the user, then re-prioritization rules can reduce the priority of reporting information about all obstacles other than the one nearest to and in front of the user, or alternatively, the re-prioritization rules can replace reporting information about all such obstacles with information that there is a field of such obstacles beginning at a distance corresponding to the closest obstacle. As a further example, if a triggering event corresponds to the approach of a person who has previously been identified to the user, the re-prioritization rules can reduce the priority or eliminate reporting of certain types of information about the person (e.g., the type of clothing worn) that has already been reported to the user at the previous identification.

After the re-prioritization rules have been retrieved in step 1250, they are applied to the refined elements of the filtered information in step 1260 to reassign the reporting priorities of these elements. The process ends at step 1270.

Returning to FIG. 2, once the refined elements have been re-prioritized in step 280, they are reported in order to the user according to their priority ranking in step 290. In general, these elements are reported to the user through a variety of signals. As discussed above in connection with FIG. 1, device 100 includes receiver-transmitters that can be used by processor 130 to transmit to the user audio and/or vibrotactile representations of the filtered and refined elements of the user's environment information. In some embodiments, device 100 communicates with an implantable prosthesis such as a visual implant to deliver representations of some of the elements—in particular, elements derived from visual information—to directly stimulate the user's ocular nerves or visual cortex.

In certain embodiments, device 100 can also transmit some of the filtered and refined elements as visual information. Many vision-impaired users are not completely blind, and their remaining vision provides an additional route to conveying information about the user's environment. Thus, processor 130 can determine, based on the nature of the various elements of information to be transmitted, which elements are best suited for transmission as visual signals. In some embodiments, processor 130 can use the receiver-transmitters to transmit certain elements both as visual signals and as other types of signals (e.g., audio and/or vibrotactile signals) to provide complementary information to the user.

A variety of different methods can be used to deliver visual signals to the user. In some embodiments, for example, displays (e.g., LCD displays) can be positioned in eyeglass frames 102 in place of the viewing lenses that would be present in an ordinary pair of glasses. These displays can be configured to receive information from processor 130, and to transmit visual representations of the information to the user via the displays. Systems and methods for transmitting visual information in this manner are disclosed, for example, in U.S. Pat. No. 8,135,227, the entire contents of which are incorporated by reference herein.

Next, in step 293, device 100 determines whether the user wishes to halt operation of the device. In general, this determination is performed by checking the status of a power button of device 100 to see whether the button has been pressed by the user, and/or determining whether the user has issued a verbal command to turn off the device. If the user has provided an indication that operation of device 100 should be halted, then the process ends at step 295. If not, then the configuration of device 100 can optionally be adjusted based on the re-prioritization rules retrieved in step 280 (as will be discussed further in connection with FIG. 13), and then control returns to step 210.

Figure 13:
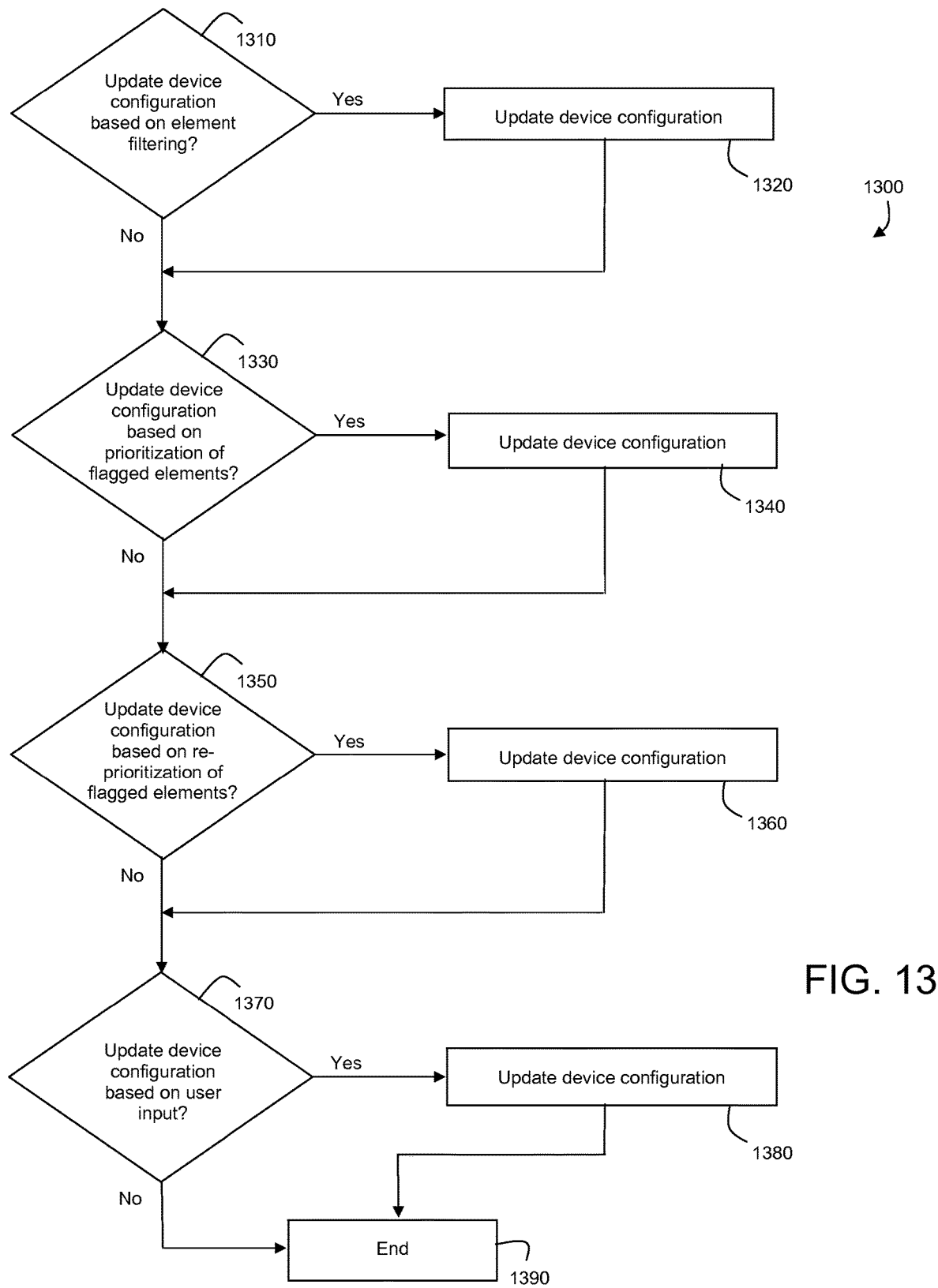
FIG. 13 is a flow chart showing steps for adjusting the configuration of a visual assistive device.

As has been discussed briefly above, the process shown in flow chart 200 can optionally adjust the configuration of device 100 at multiple points in the process to adaptively tailor the operation of the device to the user's activity. FIG. 13 is a flow chart 1300 that includes a series of steps for performing this optional adjustment. As explained above, the configuration of device 100 can be adjusted based on information obtained at various points in the process shown in FIG. 2. In step 1310, the process shown in FIG. 13 determines whether the configuration of device 100 should be updated based on the exclusionary rules retrieved in step 230 of flow chart 200. If so, the device configuration is updated at step 1320.

In general, updates to the configuration of device 100 at this stage typically include de-activating certain sensors or detectors, and/or re-configuring sensors and/or detectors to only collect certain types of information about the user's environment. Because the exclusionary rules establish that only certain elements of information will be reported to the user, in some embodiments it is no longer necessary for device 100 to continue to collect information that will not be reported. As a result, by adjusting the configuration of device 100 to avoid collection of non-reported information, the computational load on processor 130 can be reduced, and the power consumption of device 100 can also be reduced.

Next, in step 1330, the process determines whether the configuration of device 100 should be updated based on the prioritization rules retrieved in step 250 of flow chart 200. If so, the device configuration is updated at step 1340. Generally, updates to the configuration of device 100 at this stage typically include adjustments to the sensors and detectors to promote collection of information corresponding to elements that are highly prioritized, and to de-emphasize collection of information corresponding to elements with low priorities.

In step 1350, the process determines whether the configuration of device 100 should be updated based on the re-prioritization that occurs in step 280 of flow chart 200. If so, the device configuration is updated at step 1360. As in step 1350 described above, updates to the configuration of device 100 at this stage typically include adjustments to the sensors and detectors to promote collection of information corresponding to elements that are highly prioritized, and to de-emphasize collection of information corresponding to elements with low priorities. Adjusting the configuration at this stage of flow chart 1300 allows device 100 to efficiently collect information about the user's environment when the initial reporting prioritization changes due to the interaction of the user with his or her environment.

Next, in step 1370, the process determines whether the configuration of device 100 should be updated based on instructions from the user. At any time, the user can issue commands either verbally or by activating one or more of a variety of controls (e.g., touchscreens and buttons) to indicate that the configuration of device 100 should be adjusted. If processor 130 detects that the user has issued such a command, then the configuration of device 100 is updated based on the issued command in step 1380. The process then ends at step 1390.

In general, a wide variety of different adjustments to the configuration of device 100 are possible based upon information obtained during the process of FIG. 2 (e.g., exclusionary rules, prioritization rules, and re-prioritization rules) and commands issued by the user. For example, processor 130 can change the focal lengths, fields of view, apertures, integration times, gains, duty cycles, and other properties of any of the sensors and detectors in the device. Changes to the detectors and sensors can also include adjustment of the filtering elements used to acquire visual information and adjustments to post-processing algorithms applied to visual information following acquisition. For example, some or all of the detectors in the device can include variable neutral density filters, and processor 130 can be configured to select the optical density of the neutral density filter positioned in front of the sensor element of each such detector to increase or decrease an ambient light level in the collected visual information. In addition, some or all of the detectors can include variable bandpass filters, and processor 130 can be configured to select the wavelength band (e.g., the center wavelength and the bandwidth) of the bandpass filter positioned in front of the sensor element in each such detector. Some or all of the detectors can also include spatial filters or apertures which can be increased or decreased in size to restrict the field of view and/or the amount of light reaching the sensor element of each such detector. Processor 130 can adaptively adjust the spatial filter or aperture associated with each such detector to control light intensity and the field of view of the detector.

Further, to enhance collection of certain types of information, processor 130 can adjust other features of the detectors. For example, if device 100 determines that the user is engaged in the activity of reading, processor 130 can increase the resolution of detectors used to collect visual information so that text is acquired at higher resolution, facilitating the application of optical character recognition algorithms.

Processor 130 can also be configured to adjust the configuration of device 100 to account for changing operating conditions. For example, if the strength of one of the signals received by device 100 decreases (e.g., GPS), processor 130 can compensate by boosting the signal strength of another of the signals received by device 100, and when possible, can even adjust the operation of device 100 so that information that would normally be exchanged using the weaker signal is exchanged using the boosted signal, where possible. Further, processor 130 can be configured to adjust the configuration of device 100 by selecting which algorithms are used to analyze elements of the collected information, and by adjusting parameters of the selected algorithms. For example, where multiple optical character recognition algorithms are available to analyze elements that correspond to text, processor 130 can select the algorithm that works most efficiently with the collected visual information. As another example, processor 130 can adjust software-based filters that are applied to visual information collected by the detectors of device 100.

When processor 130 determines that movement of the user's eyes, head, or body has occurred, the operation of device 100 can be adjusted to compensate for such movements. For example, if processor 130 determines that the user is walking as discussed herein, then processor 130 can apply one or more filters to the visual information to compensate for involuntary motion of the detectors during walking.

If processor 130 determines that the user is voluntarily moving his or her head (e.g., as in FIGS. 4A and 4B) and/or eyes, processor 130 can alter the manner in which visual information obtained by the detectors is processed. For relatively rapid movements of either the head or eyes, processor 130 can interrupt the processing and/or transmission of elements derived from the visual information in a manner that mimics the human brain's natural visual processing response to such rapid movements, or apply algorithms to de-blur or even to eliminate the elements from the visual information prior to processing. Alternatively, for slower movements of the head or eyes, processor 130 can process the visual information and transmit elements of the information directly to the user (via receiver-transmitters 170 and 172) in a manner that conserves artifacts due to motion in the visual information. Typically, for slow movements of the head or eyes, motion artifacts are not as significant, and so they can be preserved. In this manner, motion of the detectors can be either preserved or compensated according to information measured by device 100 and the activity of the user.

Because eye, head, and body movements by the user of device 100 can all occur at the same time, processor 130 is configured to determine whether all of these types of motions are occurring, to interpret the user's actions based on the detected motions, and to adjust the configuration of device 100 accordingly. In some embodiments, for example, when movement of the head and eyes of the user occurs in the same direction and at the same speed (such as when following a slow moving object), processor 130 does not interrupt processing of visual information, and continues transmission of elements derived from the visual information to receiver-transmitters 170 and 172. Similarly, in certain embodiments, when relatively slow movement of the user's eyes occurs without corresponding head movement, processor 130 also does not interrupt processing of visual information obtained by the detectors.

Conversely, in some embodiments, when processor 130 detects rapid movement of either or both of the head and eyes of the user in the same or different directions, processor 130 can interrupt processing of visual information and/or transmission of elements derived from the information to receiver-transmitters 170 and 172, mimicking the body's natural visual-vestibular function (e.g., to avoid "retinal blur"). Processing and/or transmission remains interrupted by processor 130 until the head and eyes re-align. As above, this behavior mimics the body's natural response, where visual processing is interrupted until a stable image can be restored to the retina.

In certain embodiments, the eyes of the user can rotate inward in a convergent manner to focus on near-field objects, or rotate outward in a divergent manner to focus on far-field objects. Processor 130 can detect these movements of the user's eyes (as discussed above in connection with FIG. 1) and can adjust the configuration of the device 100 appropriately. For example, processor 130 can direct actuators 114 and/or 116 to change the orientation of detector 110 (and direct similar actuators to change the orientation of detector 112). Alternatively, or in addition, processor 130 can direct actuators 114 and/or 116 to change the focusing properties of detector 110 (e.g., the focal plane) by translating an objective lens within the detector, for example, with similar changes to detector 112 as well.

In some embodiments, the position of the user's eyes may remain relatively unchanged, even while the position of the user's head changes rapidly. This type of motion corresponds, for example, to a person shaking his or her head back-and-forth while maintaining a fixed gaze upon an object or person. When processor 130 detects such a combination of head and eye motion of the user, processor 130 can adjust the orientation of detectors 110 and 112 using actuators 114 and 116 (and corresponding actuators for detector 112) to ensure that the detectors remain oriented in a direction that corresponds with a line of sight based on the orientation of the user's eyes rather than his or her head. This emulates the influence imposed by the body's visual system over the natural vestibular-ocular reflex to rotate the eyes away from the direction of head movement.

Figure 5:
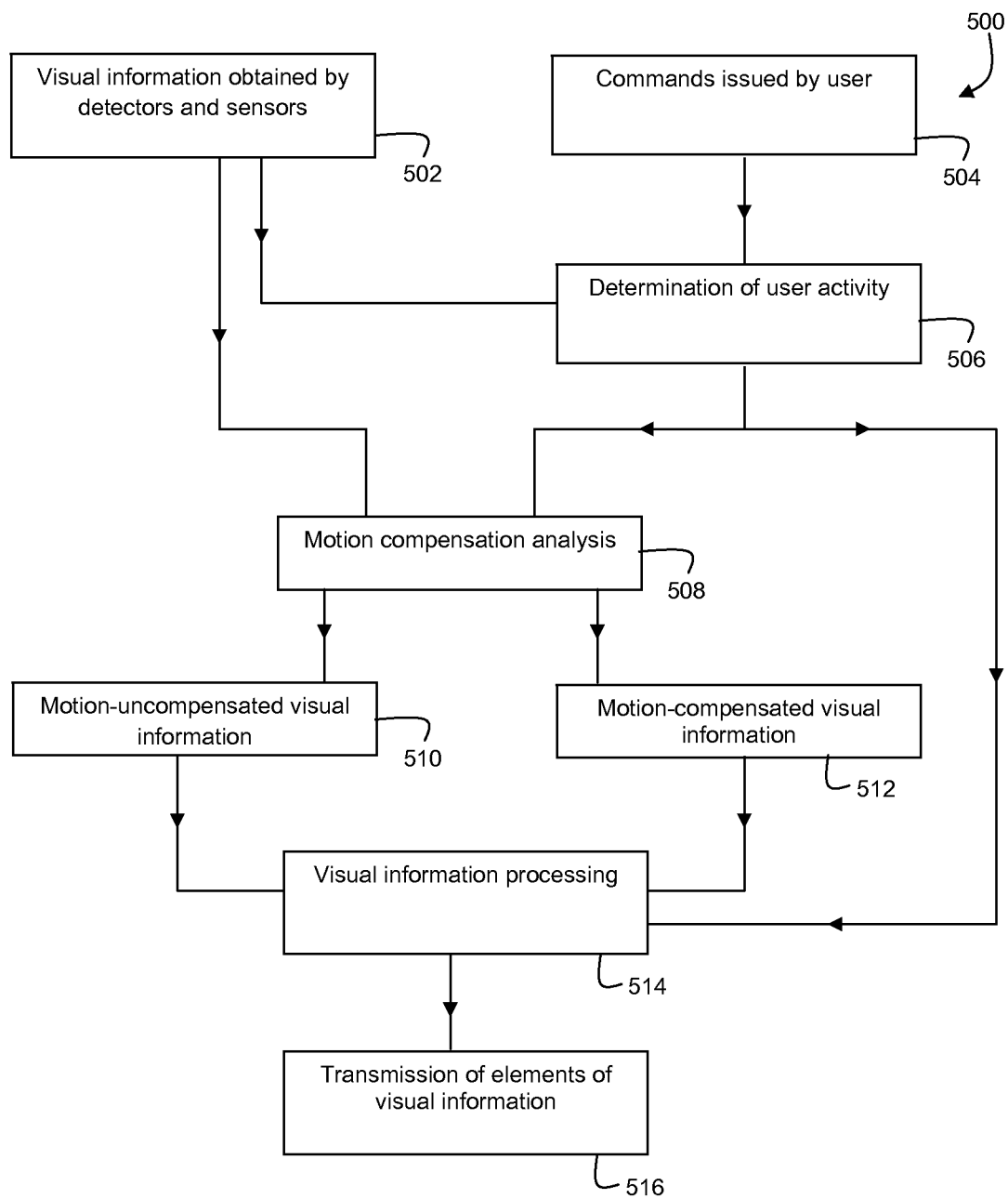
FIG. 5 is a flow chart showing steps for transmitting elements of visual information to a user of an assistive device.

FIG. 5 shows a flow chart 500 that illustrates various steps involved in transmitting elements of visual information to the user of device 100. As shown in FIG. 5, visual information obtained by the detectors and sensors in step 502 is analyzed and the results of this analysis, together with any commands issued by the user in step 504, are used by processor 130 to determine the activity of the user in step 506. Visual information is also subjected to a motion compensation analysis in step 508 to determine whether motion compensation is appropriate, based on detected movements of the user's eyes, head, and body. Visual information can either be motion-compensated (step 512) or left uncompensated (step 510), and is then processed by processor 130 in step 514 to extract various elements as discussed herein. The elements are filtered, prioritized, and then transmitted to the user of device 100 in step 516.

In addition to communicating with the various components of device 100, in some embodiments processor 130 can also communicate with external devices such as mobile phones, computing devices, and remote servers, including devices accessible to members of a medical team. Processor 130 can transmit a variety of visual and non-visual information, operational information, and diagnostic information (including, for example, parameters for evaluating the effectiveness of the assistive device) to the remote devices. In this manner, the continued usefulness of the assistive device can be evaluated without the need to test the user.

Additional information that can be transmitted includes information about the activities of the user, such as the amount of time that the user is absent from home, information about the accuracy of navigational cues provided by the device, and information about the accuracy of warnings provided by the device regarding hazards. The information can also include automated notifications if the user falls or encounters a situation that requires an emergency response by police or a medical team member. Medical team members can monitor interactions between device 100 and the user, and also communicate with the user of the device. Processor 130 allows the user to transmit an emergency signal (by voice command, for example) to request assistance.

Processor 130 can also receive software updates, configuration settings, and database information from remote devices. Transmissions to and from remote devices can be encrypted for security and to preserve patient confidentiality.

In some embodiments, the device 100 can be configured to allow continuous monitoring by a person or automated system located remotely for a monthly (or more generally, regular recurring) fee. For example, the device can be monitored in the same way that that a security system or personal alert device can be monitored, and when certain conditions are detected (e.g., when the user's body moves rapidly towards the ground and/or when the visual information obtained is consistent with a view from the ground, both of which suggest that the user has fallen), the remote person or automated system can contact the user to determine whether it is appropriate to summon assistance. The user can also contact the remote monitoring person or system directly to request assistance when needed.

IV. Use with Implantable Prosthetic Devices

As discussed herein, device 100 can be used in a system with an implantable visual prosthesis, such as a minimally invasive retinal implant, as disclosed in U.S. Pat. No. 6,976,998. A retinal or other implant can function as a receiver-transmitter in an analogous fashion to receiver-transmitters 170 and 172 on eyeglass frames 102. In particular, referring to FIG. 1 an implantable prosthetic device 190 can receive from processor 130 representations of elements of the environment information collected by device 100, after the elements have been filtered according to exclusionary rules, prioritized for reporting to the user, and re-prioritized. The implantable prosthetic device 190 can then transmit these elements directly to the user through stimulation of visual tissues or pathways.

In this manner, the prosthetic device and device 100 work together to provide the user of the system with information to interact with his or her environment, while at the same time not overwhelming the user with too much information. In particular, because the implantable prosthetic device typically provides visual and/or pseudo-visual stimuli to the user and device 100 typically provides audio and/or vibrotactile stimuli to the user, the two devices operate to provide complementary information. In many circumstances, for example, information in the form of stimuli provided by device 100 allows the user to better localize objects and people in her or his environment, while information in the form of stimuli provided by the implantable retinal prosthesis allows the user better understand the objects and people.

The operation of the implantable retinal prosthetic device is therefore controlled by processor 130 in the same manner that processor 130 controls receiver-transmitters 170 and 172. That is, the information in the form of stimuli provided by the prosthetic device to the user is controlled by processor 130, which is external to the prosthetic device. Further, the information is filtered by exclusionary rules and prioritized so that only information relevant to the user's activity is provided by the prosthetic device, in a timely fashion, and in a manner that accounts for interactions between the user and his or her environment. In addition, processor 130 can control the operation of the prosthetic device, including adjustment of the strength of stimuli applied to optical tissues, in response to commands issued by the user, for example.

Information measured by the prosthetic device can also be used to adjust the configuration of device 100. For example, if the prosthetic device is configured to measure the direction of the user's gaze, then processor 130 can use this information to re-orient the detectors of device 100, as described herein. As another example, if the prosthetic device is configured to measure changes in focusing properties of the user's eyes, processor 130 can use this information to adjust the configuration of the detectors of device 100, e.g., to change the focal plane and/or field of view of the detection optics.

V. Other Applications

A variety of additional applications of the systems and methods disclosed herein are also possible. In some embodiments, assistive device 100 can be configured to assist persons with hearing impairment. Sensors 120 and 122 can be configured to detect audio signals, and processor 130 can be configured to analyze the signals and convert the audio information therein to text. Frames 102 can include transparent displays in place of eyeglass lenses, and processor 130 can be configured to project the converted text onto the displays for viewing by the user. Processor 130 can also be configured to analyze the audio signals to identify certain sounds (e.g., sirens, horns, approaching automobiles) and display appropriate notifications and warnings to the user on the displays.

Although the disclosure herein has focused primarily on assistive devices for persons with vision impairment, the methods and systems disclosed herein can also be used for sensory augmentation of persons with no such impairments. For example, the systems disclosed herein can be implemented in a variety of wearable devices such as helmets, articles of clothing, eyewear, jewelry, and in other portable devices. The systems can be used to extend the range of information that can be perceived by the user by detecting visual information at wavelengths that humans are not ordinarily capable of seeing, by measuring audio information at intensities and frequencies that humans cannot ordinarily perceive, and by measuring positioning information that humans are incapable of otherwise measuring unaided by instruments. The information thus measured can be presented to the user in a form that the user can visualize, hear, and interpret. For example, information derived from infrared images and faint sounds detected by the system can be conveyed to a soldier wearing the system implemented as a protective helmet. Similarly, visual information can be conveyed to a fireman wearing the system implemented as a helmet to guide the fireman through burning buildings.

Additional detection methods and systems that can be used with the assistive devices disclosed herein to measure visual and other sensory information are disclosed, for example, in the following U.S. Patents and Patent Application publications, the entire contents of each of which is incorporated herein by reference: U.S. Pat. Nos. 5,521,957; 7,307,575; 7,642,949; 7,782,251; 7,898,468; 8,021,045; US 2007/0025512; and US 2008/0187104.

In some embodiments, the systems and methods disclosed herein can be used as activity monitoring devices for athletic training, rehabilitation, and mobility assessment. By implementing the monitoring devices as wearable devices (e.g., eyeglasses or sunglasses), the devices are comfortable to wear and do not interfere with daily activities. As disclosed herein, medical team members can actively monitor patients without resorting exclusively to in-person assessments to obtain timely, accurate information.

In certain embodiments, the methods and systems disclosed herein can be used more generally as human interfaces for a variety of electronic devices. For example, the assistive devices disclosed herein can be paired with mobile phones and can be used for hands-free calling, and for voice-activated internet searching.

The systems and methods disclosed herein can also be used for a variety of security applications. For example, if the user of an assistive device falls, is attacked, or is otherwise injured, the device can provide automated notifications to police or to other appropriate authorities. The assistive device can be configured both to allow the user to indicate a state of distress, and to automatically detect a state of distress of the user (for example, if the user remains motionless for a sufficiently long period of time).

VI. Other Users

Although device 100 is discussed herein with respect to a single user, device 100 can, in general, be used by multiple persons. When used by multiple persons, device 100 maintains separate configuration settings and preferences for each user, and separate databases of stored information for each user, where appropriate. For example, general navigational information can be maintained in a database that is common to all users of device 100, while navigational information that is specific to locations frequented by particular users can be maintained in user-specific databases.

To facilitate use by multiple persons, device 100 can be configured to recognize multiple users. A variety of methods can be used to implement user-specific recognition. In some embodiments, for example, users can issue a voice command to identify themselves to device 100. In certain embodiments, users can indicate their identity by activating controls on device 100, such as a button or touchscreen interface. In some embodiments, users can be equipped with an access card or module that includes a security chip (e.g., a RFID chip) that includes identifying information about the user. Device 100 can detect the access card or module automatically when the user is close to device 100.

When a particular user is identified by device 100, the device can, in certain embodiments, require that the user confirm his or her identity with a password. The user can enter the password by issuing a verbal command, or by activating a control on device 100 (e.g., a sequence of touches on a touchscreen interface or a set of buttons). Once the user has been authenticated, device 100 can automatically configure itself for operation with the authenticated user by retrieving stored user-specific configuration settings from its database, establishing connections to user-specific databases of information, and adjusting its configuration to correspond to the user-specific settings. Upon issuance of a command from the user (or when the user is too far from device 100, if authentication is proximity-based), device 100 can terminate the connections to user-specific databases and enter a standby mode until another user is authenticated.

OTHER EMBODIMENTS

A number of embodiments have been described. Nevertheless, it will be understood that various modifications may be made without departing from the spirit and scope of the disclosure. Accordingly, other embodiments are within the scope of the following claims.

What is claimed is:

1. A visual assistive device, comprising:
a detection apparatus configured to receive information about an environment surrounding a user of the visual assistive device;
a communication apparatus configured to transmit information to the user; and
an electronic processor coupled to the detection apparatus and the communication apparatus, and configured to:
obtain information about an activity of the user, wherein the information comprises at least one of a verbal or non-verbal command issued by the user and received by the electronic processor, an audio signal received by the electronic processor, a gesture of the user, and a position of the user;
filter the information about the environment surrounding the user based on the activity of the user to generate multiple elements of filtered information corresponding to a subset of the information about the environment surrounding the user;
assign a priority rank to each element of the filtered information based on the activity of the user; and
order the elements of the filtered information according to the corresponding priority ranks and transmit the ordered, filtered information to the user using the communication apparatus.

2. The device of claim 1, wherein the detection apparatus comprises at least one image detector configured to obtain images of the environment surrounding the user.

3. The device of claim 1, wherein the detection apparatus comprises at least one of a microphone, a global positioning system (GPS) sensor, a range-finding sensor, an acoustic wave sensor, and a motion sensor.

4. The device of claim 1, further comprising a housing for the detection apparatus configured to be worn on a head of the user.

5. The device of claim 1, wherein the communication apparatus comprises at least one speaker configured to transmit information to the user, and wherein the transmitted information comprises audio information derived from information received by the detection apparatus, and transmitted to the speaker by the electronic processor.

6. The device of claim 1, wherein the communication apparatus comprises at least one vibrotactile transmitter configured to contact skin of the user's body, and wherein the electronic processor is configured to transmit information to the user based on the information received by the detection apparatus, the transmitted information comprising vibrotactile signals applied to the skin of the user's body.

7. The device of claim 6, wherein the communication interface comprises:
a pair of vibrotactile transmitters positioned on opposite sides of the device, wherein the pair of transmitters are configured to transmit navigation information to the user; and
at least one additional vibrotactile transmitter, wherein the at least one additional vibrotactile transmitter is configured to transmit another type of information to the user different from navigation information,
wherein the pair of vibrotactile transmitters are configured to apply at least one of:
vibrotactile signals to the skin of the user's body at a first frequency, and the at least one additional vibrotactile transmitter is configured to apply vibrotactile signals to the skin of the user's body at a second frequency different from the first frequency; and
vibrotactile signals to the skin of the user's body at a first signal amplitude, and the at least one additional vibrotactile transmitter is configured to apply vibrotactile signals to the skin of the user's body at a second signal amplitude different from the first signal amplitude.

8. The device of claim 1, further comprising a wireless communication interface, wherein the electronic processor is coupled through the wireless communication interface to an implanted prosthetic device in the user's body and configured to transmit information to the implanted prosthetic device using the wireless communication interface.

9. The device of claim 1, wherein the elements comprise at least one of:
one or more objects in visual information received by the detection apparatus;
one or more faces in visual information received by the detection apparatus;
a position of the user in positioning information received by the detection apparatus; and
one or more portions of text in visual information received by the detection apparatus.

10. The device of claim 1, wherein prior to transmitting the ordered filtered information to the user, the electronic processor is configured to further process the filtered information by assigning an identity to elements that correspond to faces in visual information received by the detection apparatus.

11. The device of claim 10, wherein the electronic processor is further configured to refine the elements of the filtered information by transmitting the elements to a remote electronic processor that refines the elements, and receiving information corresponding to the refined elements from the remote electronic processor.

12. The device of claim 1, wherein prior to transmitting the ordered filtered information to the user, the electronic processor is configured to further process the filtered information by assigning an identity to elements that correspond to objects in visual information received by the detection apparatus.

13. The device of claim 1, wherein prior to transmitting the ordered, filtered information to the user, the electronic processor is configured to assign an identity to a human speaker of elements that correspond to speech.

14. The device of claim 1, wherein the electronic processor is configured to assign a priority rank to each element of the filtered information by assigning a first priority rank to elements of the filtered information that correspond to hazards in the environment surrounding the user.

15. The device of claim 14, wherein the electronic processor is configured to assign a priority rank lower than first to elements of the filtered information that correspond to signs, buildings, landmarks, location signals from embedded radiofrequency tags, and navigational instructions.

16. The device of claim 1, wherein the activity of the user is reading, and wherein the electronic processor is configured to assign a highest priority rank to elements of the filtered information that correspond to headlines and titles, and a lower priority rank to elements of the filtered information that correspond to other text.

17. The device of claim 1, wherein the electronic processor is configured to assign the priority rank to each element corresponding to an object in visual information received by the detection apparatus based on at least one of a distance between the object and the user, and an angular relationship between the object and a direction in which the user is oriented.

18. A visual assistive system, comprising:
the device of claim 1; and
a visual prosthetic device, embedded: in, or in proximity to, an eye of the user; or in, or in proximity to, an optic nerve of the user; or within, along, or in proximity to a visual pathway or visual region of a brain of the user,
wherein the electronic processor is configured to transmit at least some of the elements of the filtered information derived from visual information received by the detection apparatus to the visual prosthetic device; and
wherein the visual prosthetic device is configured to transmit a representation of each of the transmitted elements to at least one of the eye of the user, the optic nerve of the user, and the visual pathway or visual region of the brain of the user.

19. The device of claim 1, wherein the electronic processor is configured to adjust a configuration of the detection apparatus prior to receiving at least some of the information about the environment surrounding the user.

20. The device of claim 19, wherein the electronic processor is configured to:
determine components of motion of the user in visual information received by the detection apparatus; and
adjust the configuration of the detection apparatus to compensate for at least some of the components of motion.

21. A method for providing environmental information to a visually impaired subject, the method comprising:
receiving information about an environment surrounding the subject;
determining an activity of the subject based on at least one of a received verbal or non-verbal command issued by the subject, a received audio signal, a gesture of the subject, and a position of the subject;
filtering the information about the environment surrounding the subject based on the subject's activity to generate multiple elements of filtered information corresponding to a subset of the information about the environment surrounding the subject;
assigning a priority rank to each element of the filtered information based on the subject's activity; and
ordering the elements of the filtered information according to the corresponding priority ranks and transmitting the ordered, filtered information to the subject.

22. The method of claim 21, wherein filtering the information about the environment surrounding the subject based on the subject's activity comprises filtering the information based on one or more threshold conditions associated with the activity of the subject.

23. The method of claim 21, further comprising, prior to assigning the priority ranks, identifying one or more of the elements of the filtered information, wherein identifying one or more of the elements of the filtered information comprises at least one of locating objects in visual information about the environment surrounding the subject, locating faces in visual information about the environment surrounding the subject, determining a position of the subject relative to the environment surrounding the subject, and locating portions of text in the visual information about the environment surrounding the subject.

24. The method of claim 21, further comprising, prior to transmitting the ordered, filtered information to the subject, further processing the elements of the filtered information to refine the elements, wherein refining the elements comprises at least one of assigning an identity to elements that correspond to faces in visual information about the environment surrounding the subject, assigning an identity to elements that correspond to objects in visual information about the environment surrounding the subject, assigning an identity to a speaker of elements that correspond to speech in audio information about the environment surrounding the subject, and identifying a color associated with elements that correspond to objects in visual information about the environment surrounding the subject.

25. The method of claim 21, wherein assigning a priority rank to each element of the filtered information comprises assigning a first priority rank to elements of the filtered information that correspond to hazards in the environment surrounding the subject, and assigning a priority rank lower than first to elements of the filtered information that correspond to signs, buildings, landmarks, location signals from embedded radiofrequency tags, and navigational instructions.

26. The method of claim 21, further comprising, for each element corresponding to an object in the environment surrounding the subject, assigning the element's priority rank based on at least one of a distance between the object and the subject, and an angular relationship between the object and a direction in which the subject is oriented.

27. The device of claim 1, wherein prior to transmitting the ordered filtered information, the electronic processor is configured to:
re-assess the priority ranks of one or more elements of the filtered information; and
transmit the ordered, filtered information according to the re-assessed priority ranks.

28. The device of claim 27, wherein the electronic processor is configured to:
determine whether a triggering event for re-assessment of the priority ranks has occurred prior to transmitting the filtered information; and
re-assess the priority ranks only if a triggering event has occurred.

29. The device of claim 27, wherein the electronic processor is configured to re-assess the priority ranks by retrieving a set of rules from a database based on the activity of the user, and applying the set of rules to the elements of the filtered information.

* * * * *

UNITED STATES PATENT AND TRADEMARK OFFICE
CERTIFICATE OF CORRECTION

PATENT NO. : 10,571,715 B2
APPLICATION NO. : 14/356071
DATED : February 25, 2020
INVENTOR(S) : Joseph F. Rizzo, III et al.

Page 1 of 1

It is certified that error appears in the above-identified patent and that said Letters Patent is hereby corrected as shown below:

In the Claims

In Column 44, Line 27, Claim 10, delete "ordered" and insert -- ordered, --

In Column 44, Line 39, Claim 12, delete "ordered" and insert -- ordered, --

In Column 46, Line 38 (approx.), Claim 27, delete "ordered" and insert -- ordered, --

Signed and Sealed this
Eighth Day of December, 2020

Andrei Iancu
*Director of the United States Patent and Trademark Office*